(12) United States Patent
Honda et al.

(10) Patent No.: US 6,800,433 B1
(45) Date of Patent: Oct. 5, 2004

(54) PROCESS FOR PURIFICATION OF PROANTHOCYANIDIN OLIGOMER

(75) Inventors: Shinkichi Honda, Chiyoda-ku (JP); Tomoya Takahashi, Tsukuba (JP); Ayako Kamimura, Tsukuba (JP); Takako Matsuoka, Yokkaichi (JP); Tomomasa Kanda, Hirosaki (JP); Akio Yanagida, Hachioji (JP); Kazuo Hieda, Kashiwa (JP)

(73) Assignees: Kyowa Hakko Kogyo Co., Ltd., Tokyo (JP); The Nikka Whisky Distilling Co., Ltd., Tokyo (JP)

(*) Notice: Subject to any disclaimer, the term of this patent is extended or adjusted under 35 U.S.C. 154(b) by 0 days.

(21) Appl. No.: 09/959,274

(22) PCT Filed: Mar. 3, 2000

(86) PCT No.: PCT/JP00/01307
§ 371 (c)(1),
(2), (4) Date: Oct. 19, 2001

(87) PCT Pub. No.: WO00/64883
PCT Pub. Date: Nov. 2, 2000

(30) Foreign Application Priority Data

Apr. 23, 1999 (JP) .......................................... 11/116380

(51) Int. Cl.⁷ ............................ C12Q 1/00; C12Q 1/34; C12Q 1/44

(52) U.S. Cl. ................................ 435/4; 435/18; 435/19
(58) Field of Search ................................ 435/4, 18, 19

(56) References Cited

U.S. PATENT DOCUMENTS

| | | | |
|---|---|---|---|
| 4,698,360 A | 10/1987 | Masquelier | 424/195.1 |
| 4,797,421 A * | 1/1989 | Ariga et al. | 420/545 |
| 5,484,594 A | 1/1996 | Frangi et al. | 424/195.1 |
| 5,554,645 A * | 9/1996 | Romanczyk et al. | 514/453 |
| 5,773,262 A | 6/1998 | Ariga et al. | 435/118 |
| 5,804,192 A | 9/1998 | Franc et al. | 424/195.1 |
| 5,814,494 A | 9/1998 | Ariga et al. | 435/118 |
| 6,015,913 A * | 1/2000 | Kealey et al. | 549/386 |

FOREIGN PATENT DOCUMENTS

| | | |
|---|---|---|
| EP | 0 692 480 | 1/1996 |
| JP | 3-200781 | 9/1991 |
| JP | 7-62014 | 7/1995 |
| JP | 10-218769 | 8/1998 |
| WO | 97/39632 | 10/1997 |
| WO | 97/44407 | 11/1997 |

OTHER PUBLICATIONS

Lea, "The Phenolics of Ciders: Oligomeric and . . . ", J. Sci. Fd. Agric., vol. 29 (1978), pp. 471–477.

(List continued on next page.)

Primary Examiner—Louise N. Leary
(74) Attorney, Agent, or Firm—Fitzpatrick, Cella, Harper & Scinto

(57) ABSTRACT

The present invention relates to a process for purifying dimeric to pentameric proanthocyanidin oligomers which comprises extracting the proanthocyanidin oligomers from raw materials containing the proanthocyanidin oligomers or crude purification products therefrom by solid-liquid extraction using methyl acetate as a liquid phase; a process for purifying dimeric to pentameric proanthocyanidin oligomers which comprises pretreating with an enzyme for hydrolysis raw materials containing the proanthocyanidin oligomers, crude purification products therefrom, or a solution containing one of these; and a process for purifying dimeric to pentameric proanthocyanidin oligomers with a uniform polymerization degree which comprises separating and purifying the proanthocyanidin oligomers by polymerization degree from raw materials containing the proanthocyanidin oligomers or crude purification products there from by normal phase silica gel liquid chromatography using as a mobile phase a single solvent or a mixed solvent of two or more solvents selected from the group consisting of an ester solvent, a ketone solvent, a hydrocarbon solvent, an ether solvent and an alcohol solvent.

32 Claims, 16 Drawing Sheets

OTHER PUBLICATIONS

Rigaud, et al., "Normal–phase high–performance liquid chromatographic separation . . . ", Journal of Chromatology A, vol. 654 (1993), pp. 255–260.

Prieur, et al., "Oligomeric and Polymeric Procyanidins from Grape Seeds", Phytochemistry, vol. 36, No. 3 (1994), pp. 781–784.

Cui, et al., "Constituents of a Fern, *Davallia mariesii*, Moore. I. Isolation and Structures of . . . ", Chem. Pharm. Bull., vol. 38, No. 12 (1990), pp. 3218–3225.

Mohammed R. Koupai–Abyzani et al., "Purification and Characterization of a Proanthoacyanidin Polymer from Seed of Alfalfa (Medicago sativa Cv. Beaver)", American Chemical Society, vol. 41, pp. 565–569 (1993).

Cui, et al., Constituents of a Fern, *Davallia mariesii*, Moore. II. "Identification and $^{1}$H– and $^{13}$C–Nuclear . . . ", Chem. Pharm. Bull., vol. 40, No. 4 (1990), pp. 889–898.

Matsuo, et al., "A Simple and Rapid Purification Method of Condensed Tannins . . . ", Agric. Biol. Chem., vol. 45, No. 8 (1981), pp. 1885–1887.

Nonaka, et al., "Tannins and Related Compounds. A New Class of Dimeric . . . ", Chem. Pharm. Bull, vol. 31 (1983), pp. 3906–3914.

Hashimoto, et al., "Tannins and Related Compounds. LXXVII. Novel Chalcan–flavan Dimers . . . ", Chem. Pharm. Bull, vol. 37, No. 1 (1989), pp. 77–85.

Kahiwada, et al., "Tannins and Related Compounds. XLV. Rhubard, (5). Isolation and . . . ", Chem. Pharm. Bull., vol. 34 (1986), pp. 3208–3222.

Gariboldi, et al., "LC–UV–Electrospray–MS–MS Mass . . . ", Pharmaceutical Research, vol. 15, No. 6 (1998), pp. 936–943.

Hammerstone, "Identification of Procyanidins in Cocoa . . . ", J. Agric. Food Chem., vol. 47 (1999), pp. 490–496.

* cited by examiner

F I G. 1
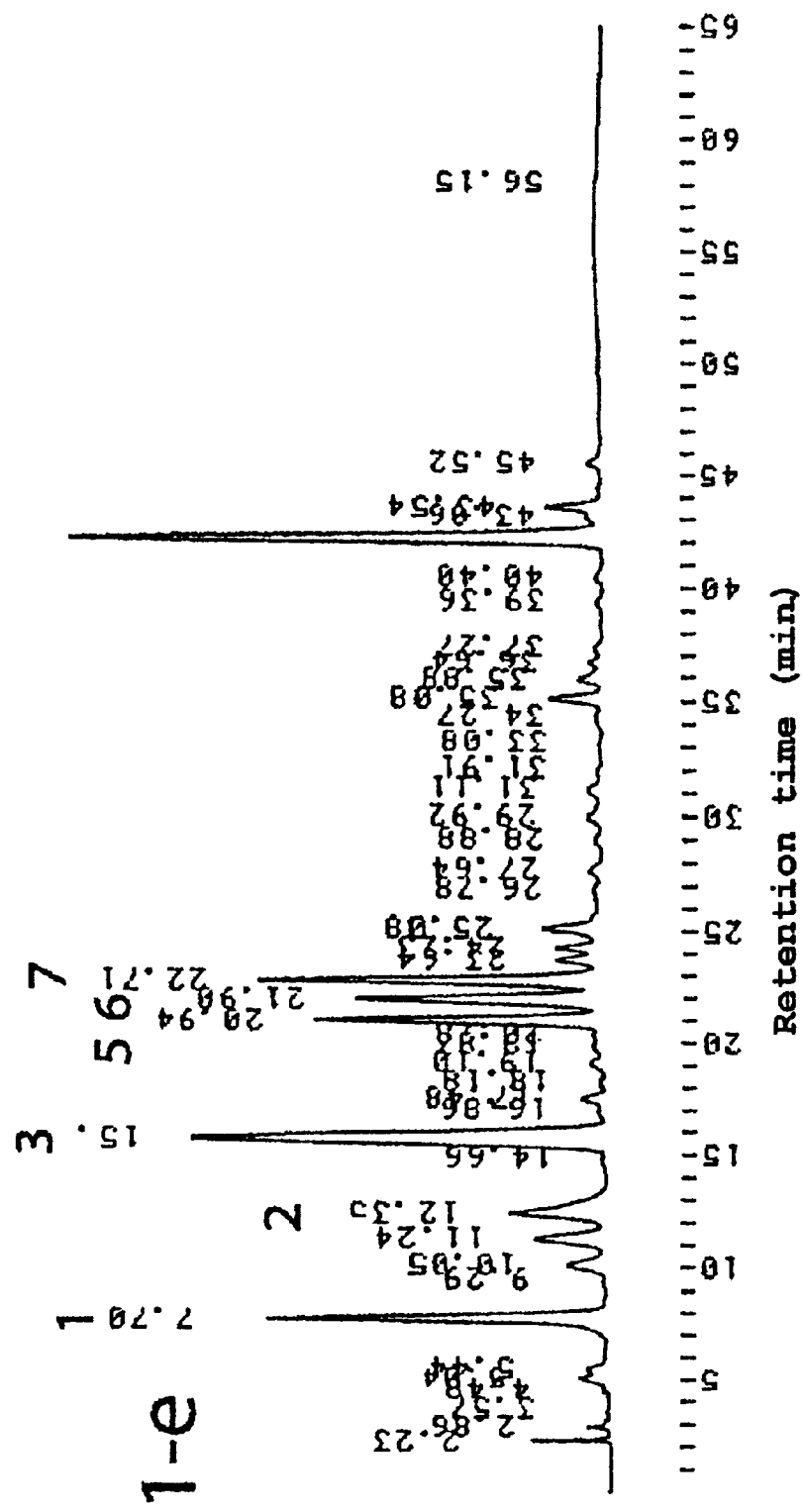

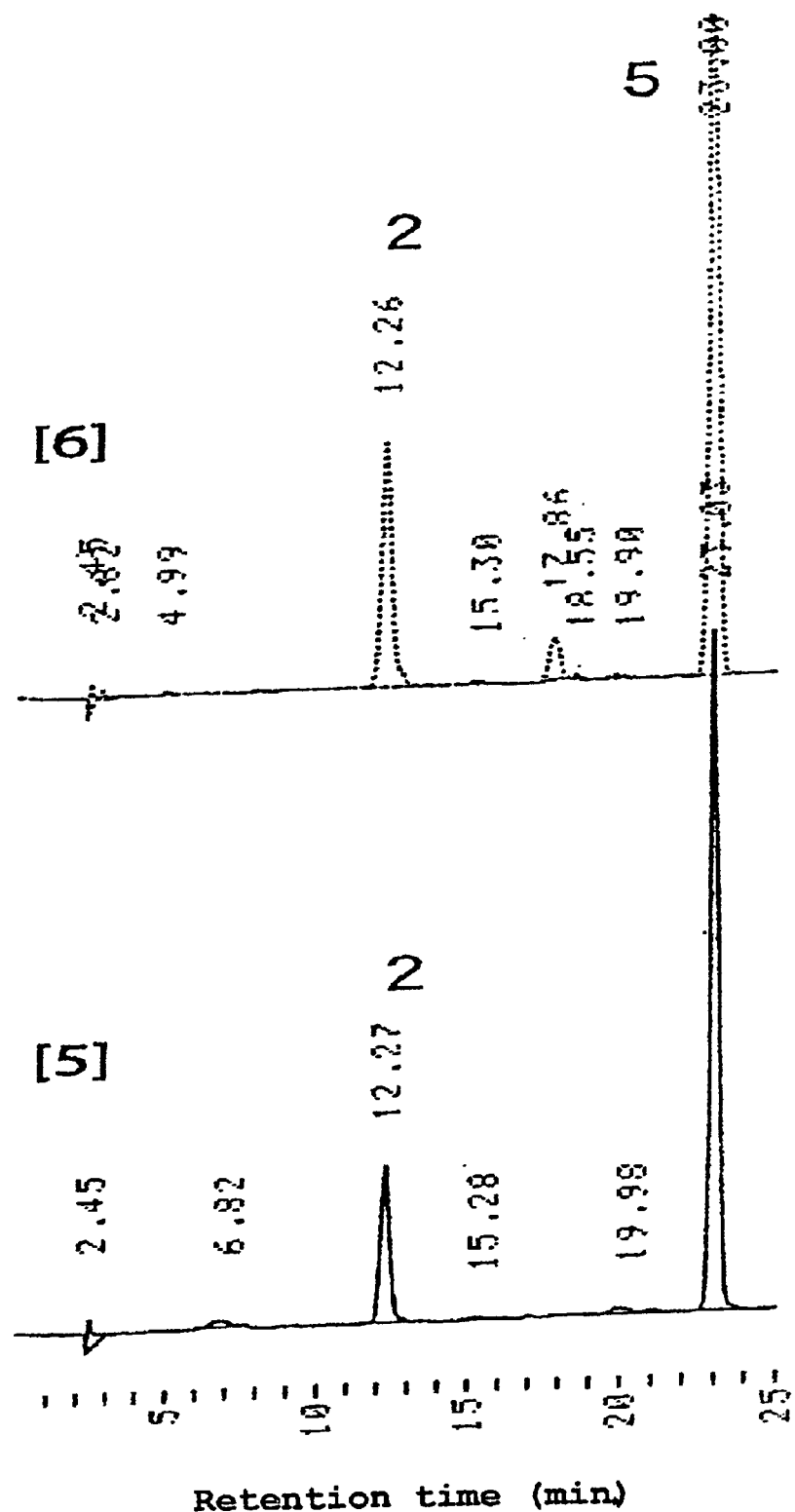

PROCESS FOR PURIFICATION OF PROANTHOCYANIDIN OLIGOMER

TECHNICAL FIELD

The present invention relates to a process for efficiently purifying proanthocyanidin oligomers with high purity which have a variety of biological activities including antitumor, anti-inflammatory, anti-aging, antioxidant, antiallergy, antibacterial, and hair growth activities, and can usefully be applied to foods, cosmetics, drugs or the like.

BACKGROUND ART

Generally, proanthocyanidin, which is known as a biophylaxis substance of higher plants, is a generic name for polymers in the form of a dimer or higher order which are polymerized by binding formats, such as 4β→6, 4β→8, 4β→8·2βO→7, with flavan-7-ol as a constitutional unit. These are also called condensed tannins, ("E. Steinegger & R. Hänsel, Pharmacognosy [$1^{st}$ vol.], Approach to Chemistry and Pharmacology" (Translated by Shuji Itokawa et al., Hirokawa Publishing Co.), 204–208 (1977); Porter L. J., Flavans and proanthocyanidins, In: Harborne, J. B. (ed.), "The Flavonoids, Advances in Research Science 1986", Chapman & Hall, 23–55 (1994)). These are generally called proanthocyanidin because they produce anthocyanidin and turn red by acid treatment. Proanthocyanidins are known to show a variety of biological activities. The activities that have been reported include antitumor, anti-inflammatory, anti-aging, antioxidant, antiallergy, antibacterial, and hair growth activities [Bart Schwitters/Jack Masquelier, "$21^{st}$ century Biophylaxis Substance OPC", translated by Akira Sasaki, Fragrance Journal, 50–135 (1997); Tomoya Takahashi, et al., Journal of Investigative Dermatology, 112, 310–316 (1999)]. Not all the relationships between structure and activity, between these biological activities and the degree of polymerization of proanthocyanidins have been clarified. For example, regarding hair growth activity, dimeric to pentameric proanthocyanidin oligomers (especially dimer and trimer) in proanthocyanidins have been reported to have the highest activity (WO96/00561).

Regarding separation and purification of proanthocyanidins from plant bodies, attempts have been made to separate and purify proanthocyanidins from various plant bodies including grape seeds, pine barks, ginkgo leaves, peanuts, and cocoa beans. Examples of industrial extraction from raw materials in these include the extraction from grape seeds (Japanese Published Unexamined Application No.3-200781, WO97/39632, U.S. Pat. No. 5,484,594), pine bark (U.S. Pat. No. 4,698,360,WO97/44407) or the like. In the method according to Japanese Published Unexamined Application No.3-200781, a pretreatment is performed by allowing white grape seeds to contact with water at less than 70° C., followed by extraction by hot water. The resulting extract is applied to a Sephadex LH-20™ column, and then eluted with 70% ethanol, thereby obtaining proanthocyanidins-containing powder with a purity of approximately 90%. In the method according to U.S. Pat. No. 4,698,360, 1 ton of pinaster bark is subjected to hot water extraction under pressure, and then ethyl acetate elution and precipitation by addition of chloroform are repeated, so that proanthocyanidins-containing powder is obtained. However, none of the purified products resulting from the above methods contains 90% or more of dimeric to pentameric proanthocyanidin oligomers only. All of these purified products also contain monomers, hexameric or higher order polymers, or other organic acids.

As a process for purifying proanthocyanidins using the counter current liquid-liquid distribution method, for example, a method using water and ethyl acetate is described in Andrew G. H. Lea, J. Sci. Fd. Agric., 29, 471–477 (1978), in Japanese Published Unexamined Application No.61-16982 and the like.

As a process for purifying proanthocyanidins using solid-liquid extraction, for example, a method using ethyl acetate is described in Japanese Published Unexamined Application No.8-176137 and EP0707005.For example, 100 kg of crushed grapes are extracted with a mixed solvent of water (1650L), sodium chloride (300 kg) and acetone (550L). Next, acetone is removed by distillation so as to obtain the residue. The residue is then subjected to solid-liquid extraction using ethyl acetate, and then dichloroethane (45L) is added thereto, thereby obtaining 1.5 kg to 2.5 kg of a proanthocyanidin precipitate (EP0707005)

Further, known methods for purifying proanthocyanidins using chromatography include a method using the above Sephadex LH-20™ column (a method for extraction from grape seeds, Japanese Published Unexamined Application No.3-200781), and a method using polystyrene-based adsorption resin (a method for extraction from red beans, Japanese Published Examined Application No. 7-62014). For example, polystyrene polystyrene-based resin "Sepabeads SP-850™ "(MITSUBISHI CHEMICAL CORPORATION) is added to water obtained by immersing dried red beans therein and the mixture is stirred, thereby allowing proanthocyanidins to adsorb thereto. Then, the resin is dried at less than 70° C., and then eluted with 80% (v/v) ethanol at 70° C., so that crude proanthocyanidins-containing powder with a purity of approximately 60% can be obtained.

However, all of these processes are for purifying proanthocyanidin mixtures independent of polymerization degree. That is, these processes are not for efficiently and selectively obtaining dimeric to pentameric proanthocyanidin oligomers. Their recovery rate of dimeric to pentameric proanthocyanidin oligomers is low.

Regarding separation of proanthocyanidins by polymerization degree, a method using normal phase silica gel liquid chromatography is known (A method for extraction from cocoa beans: J. Rigaud et al., J. Chromatogr. A, 654, 255–260 (1993), A method for extraction from grape seeds: Corine Prieur et al., Phytochemistry, 36, 781–784 (1994)). The former method comprises loading a sample solution containing proanthocyanidins, which has been obtained by methanol extraction from cocoa beans, into a silica gel column, followed by gradient elution using a mixed solvent of dichloromethane:methaol:formic acid:water [(41→5): (7→43):1:1] as a mobile phase. The latter method comprises loading a sample solution containing proanthocyanidins, which has been obtained by methanol extraction from grape seeds, into a silica gel column, followed by gradient elution using a mixed solvent of dichloromethane:methanol:water-:trifluoroacetic acid [(82→10):(18→86):2:0.05] as a mobile phase.

However, these methods involve problems such that recovery and reuse of solvents are difficult because of the use of a solvent containing chlorine and the complication of a solvent composition. Further, gradient elution to apply concentration gradients to a mobile phase is required. Therefore, these methods are not appropriate for mass purification-oriented industrial separation methods in view of safety and economy.

DISCLOSURE OF THE INVENTION

The object of the present invention is to provide processes for efficiently purifying dimeric to pentameric proanthocyanidin oligomers with high purity from raw materials containing proanthocyanidins or crude purification products therefrom.

A combination of conventional techniques is not good enough to remove substances other than the target components being dimeric to pentameric proanthocyanidin oligomers, for example monomers constituting proanthocyanidins, such as flavonoids, catechin or epicatechin, hexameric or higher order high polymeric proanthocyanidin polymers, or other contaminants. That is, it is difficult to efficiently obtain with high purity dimeric to pentameric proanthocyanidin oligomers, which are target components of this invention. In addition, most of known methods are not appropriate for industrial processes in view of the complication of a solvent composition used, economy, safety or the like.

As a result of thorough studies to solve these problems, we have completed a process for efficiently purifying dimeric to pentameric proanthocyanidin oligomers with high purity.

The first embodiment is a process for purifying dimeric to pentameric proanthocyanidin oligomers, which comprises extracting the proanthocyanidin oligomers by a solid-liquid extraction method using methyl acetate as a liquid phase from raw materials containing the proanthocyanidin oligomers or crude purification products therefrom.

As the above liquid phase, methyl acetate may be used as a single solvent or a mixed solvent, being a combination of methyl acetate and an organic solvent miscible with methyl acetate, which is prepared by adding such an organic solvent to methyl acetate.

The second embodiment is a process for purifying dimeric to pentameric proanthocyanidin oligomers which comprises pretreating with an enzyme for hydrolysis raw materials containing the proanthocyanidin oligomers, crude purification products therefrom, or a solution containing one of these.

The third embodiment is a process for purifying dimeric to pentameric proanthocyanidin oligomers with a uniform polymerization degree, wherein the proanthocyanidin oligomers are separated and purified by polymerization degree from raw materials containing the proanthocyanidin oligomers or crude purification products therefrom by normal phase silica gel liquid chromatography using as a mobile phase a single solvent or a mixed solvent of two or more solvents selected from the group consisting of an ester solvent, a ketone solvent, a hydrocarbon solvent, an ether solvent and an alcohol solvent. Preferably, a mixed solvent of two or more solvents is used as the above mobile phase.

Further, the present invention can provide purified dimeric to pentameric proanthocyanidin oligomers with a purity of 90(w/w) % or more, dimeric proanthocyanidins with a purity of 90(w/w) % or more, and trimeric proanthocyanidins with a purity of 90(w/w) % or more, which are obtainable by the above purification processes or a combination thereof.

Proanthocyanidins are condensed tannins present in various plant bodies and possess a basic structure wherein flavan-7-ol is sequentially condensed or polymerized by binding of 4β→6, 4β→8, 4β→8·2βO→7 or the like. In this specification, dimers to pentamers of proanthocyanidins and hexamers or higher order polymers of proanthocyanidins are defined as proanthocyanidin oligomers and proanthocyanidin polymers, respectively. Moreover, a flavan-7-ol monomer is defined as a monomer constituting proanthocyanidins. Examples of proanthocyanidin oligomers include proanthocyanidins, such as procyanidin, prodelphinidin, and propelargonidin, and all the stereoisomers thereof. A monomer constituting proanthocyanidins is shown by the following formula (I):

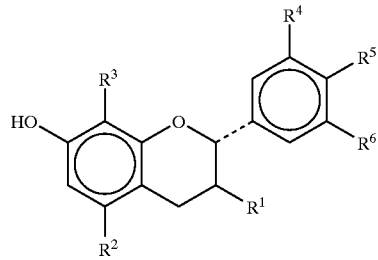

(wherein $R^1$, $R^2$, $R^3$, $R^4$, $R^5$ and $R^6$ are the same or different and represent hydrogen, a hydroxyl group or a galloyl group).

Examples of raw materials or crude purification products therefrom used in this invention include any which contain proanthocyanidin oligomers, and particularly preferable examples of these include plant raw materials, such as fruits, seedvessels, seeds and barks of plants, extracts therefrom, and crude purification products therefrom. For example, those rich in the content of proanthocyanidin oligomers are preferable, including juice of fruits, or extracts from seedvessels or seeds, of grapes, persimmons, apples, blueberries, cranberries or the like; or extracts from epidermis of peanuts, chestnuts or the like, husks of barley bran or buckwheat, leaves of persimmon, pine bark, palm, or the like.

Furthermore, crude products or crude purification products therefrom obtained by non-enzymatic or enzymatic methods can also be used as raw materials. Examples of a synthetic process for synthesizing proanthocyanidin oligomers include a manufacturing process for a dimer of epicatechin or catechin described in Journal of Chemical Society Perkin Transaction I, 1535–1543 (1983) and a manufacturing process for a trimer of epicatechin or catechin described in Phytochemistry, 25, 1209–1215 (1986). Crude products or crude purification products therefrom obtained by or in a manner similar to these processes can also be used as raw materials for the process of this invention.

A volatile organic solvent is preferable as the organic solvent miscible with methyl acetate used for the first embodiment. Examples of such organic solvents include alcohol solvents, such as methanol, ethanol, propanol, and butanol; ester solvents, such as methyl formate, ethyl formate, and ethyl acetate; ketone solvents, such as acetone; nitrile solvents, such as acetonitrile; ether solvents, such as tetrahydrofuran and 1,2-dimethoxyethane; hydrocarbon solvents such as hexane; and carboxylic acid solvents such as acetic acid. When an organic solvent miscible with methyl acetate is used, the entire extraction solvent preferably contains methyl acetate 50% (volume) or more, more preferably 70% (volume) or more, and still more preferably 90% (volume) or more.

Examples of the enzyme for hydrolysis used in the second invention include glycosidase and esterase.

Examples of the enzyme for hydrolysis used in the second invention include glycosidase, and esterase.

Examples of glycosidase include a single substance or a mixture of two or more substances selected from the group consisting of amylase, cellulase, glucanase, xylanase, glucosidase, dextranase, chitinase, galacturonase, lysozyme, galactosidase, mannosidase, fructofuranosidase, trehalase, glucosaminidase, pullulanase, ceramidase, fucosidase, and agarase. Examples of esterase include a single substance or a mixture of two or more substances selected from the group consisting of carboxyesterase, arylesterase, lipase, acetylesterase, cholinesterase, pectinesterase, cholesterol esterase, chlorophyllase, lactonase, tannase, and hydrolase.

In the second embodiment, examples of the solution containing raw materials containing dimeric to pentameric proanthocyanidin oligomers or crude purification products therefrom generally include an aqueous solution, or an aqueous solution containing 10% or less of an organic solvent, such as an alcohol, ester, or ketone.

In the third embodiment, examples of the ester solvent used as a mobile phase include methyl formate, ethyl formate, propyl formate, isopropyl formate, butyl formate, isobutyl formate, methyl acetate, ethyl acetate, propyl acetate, isopropyl acetate, butyl acetate, isobutyl acetate, methyl propionate, ethyl propionate, propyl propionate, isopropyl propionate, butyl propionate, isobutyl propionate, methyl butyrate, ethyl butyrate, propyl butyrate, isopropyl butyrate, butyl butyrate, and isobutyl butyrate. Examples of the ketone solvent include acetone, methyl ethyl ketone, methyl propyl ketone, methyl isopropyl ketone, methyl butyl ketone, methyl isobutyl ketone, methyl tert-butyl ketone, diethyl ketone, diisopropyl ketone, methyl vinyl ketone, cyclobutanone, cyclopentanone, and cyclohexanone. Examples of the hydrocarbon solvent include pentane, hexane, heptane, octane, nonane, decane, nonadecane, cyclohexane, xylene, and toluene. Examples of the ether solvent include tetrahydrofuran and 1,2-dimethoxyethane. Examples of the alcohol solvent include methanol, ethanol, propanol, isopropanol, butanol, sec-butanol, tert-butanol and the like.

Extraction and rough purification from plant raw materials can be performed, for example, by known processes as described below.

Plant raw materials including plant fruits, seedvessels, seeds, coats, husks, leaves, and barks are used as materials for extraction after a drying process such as air drying generally. The intact plant raw materials may also be used as materials for extraction.

Rough extraction of proanthocyanidins from the above materials for extraction can be performed with reference to known processes [Chem. Pharm. Bull., 38, 3218 (1990), Chem. Pharm. Bull., 40, 889–898 (1992)]. For example, crushed or shredded plant raw materials are subjected to extraction using a solvent. As the solvent for extraction, a single or a mixed solvent of two or more solvents selected from a hydrophilic solvent and a lipophilic solvent may be used. Such solvents include water, alcohol solvents such as methanol, ethanol and isopropanol, ketone solvents such as acetone and methyl ethyl ketone, and ester solvents such as methyl acetate and ethyl acetate. A temperature for extraction generally ranges from 0 to 100° C., preferably 5 to 50° C. A material such as a seed which contains oil may be subjected as such to extraction without crushing. Extraction may be repeated two to three times, if necessary. The insoluble residue is removed by filtration or centrifugation from the rough extract solution obtained by the above step, obtaining a rough extract solution. Plant raw materials, such as plant juice, sap or the like, maybe directly used as materials for extraction, or a concentrated rough extract solution of condensed tannins maybe prepared with reference to Agric. Biol. Chem., 45, 1885–1887 (1981).

Extraction and rough purification from rough products obtained by a chemical method, such as non-enzymatic or enzymatic methods, may also be performed in a manner similar to those described above.

Next, a detailed description of the purification process of this invention will be given with examples.

In the first invention, dimeric to pentameric proanthocyanidin oligomers are purified by subjecting raw materials containing the proanthocyanidin oligomers or crude purification products therefrom to solid-liquid extraction using either a single solvent of methyl acetate or a mixed solvent of methyl acetate and an organic solvent miscible with methyl acetate as a liquid phase. When raw materials or crude purification products therefrom are liquid, previous solidification by spray-drying or freeze-drying is preferably performed. Generally, the mixture ratio (w/v) of a solid and methyl acetate, or of a solid and a mixed solvent of methyl acetate and an organic solvent miscible with methyl acetate is approximately 1:1 to 1:1000. Extraction is performed at room temperature or by heating with stirring for a short period of time. Preferably, the mixture ratio (w/v) of a solid and methyl acetate, or of a solid and a mixed solvent of methyl acetate and an organic solvent miscible with methyl acetate is 1:5 to 1:100. Extraction at room temperature for approximately 1 hour, and the subsequent repeated extraction (several times) of the residue under the same conditions are more preferred. A finer particle size of powder is preferred for efficient solid-liquid extraction. When extraction is performed using a mixed solvent, it is preferable that the mixed solvent has solvent polarity analogous to that of methyl acetate by mixing the solvents. The solid-liquid extraction using these solvents suppresses elution of proanthocyanidin polymers and other contaminants, and enables efficient purification of dimeric to pentameric proanthocyanidin oligomers. In the first embodiment, dimeric to pentameric proanthocyanidin oligomers may be recovered by freeze-drying or spray drying after concentrating the resulting methyl acetate extract and dissolving again the concentrated residue in water or in an aqueous solvent such as a buffer.

In the second embodiment, dimeric to pentameric proanthocyanidin oligomers are purified by pretreating with an enzyme for hydrolysis raw materials containing the proanthocyanidin oligomers, crude purification products therefrom, or a solution containing one of these. The raw materials or crude purification products therefrom generally contain many contaminants other than proanthocyanidin oligomers. Particularly, when the raw materials or crude purification products therefrom are derived from plants, polyphenol glycosides, esters or the like, besides proanthocyanidin oligomers, are present in a high proportion. Pretreatment of such glycosides or esters, which are contaminants, with the above hydrolase to obtain aglycon enables efficient removal of the contaminants at the next purification step and improvements in purity of proanthocyanidin oligomers. For example, by treatment with β-glycosidase, rutin, which is a flavonoid glucoside abundant in a whole plant of *Fagopyrum esculentum* of the family Polygonaceae, results in quercetin being aglycon. When chlorogenic acid and p-coumaroylquinic acid, which are hydroxycinnamates and contained richly in fruits or leaves of dicotyledons, are treated with hydroxycinnamate hydrolase, their depside bonds, which are intramolecular ester bonds, are hydrolyzed, resulting in caffeic acid and quinic acid, and p-coumaric acid and quinic acid, respectively. Reaction conditions for treatment with the enzyme for hydrolysis differ depending on the type of enzymes or the like. Generally, conditions are pH 3 to 8, 25 to 55° C., and 1 to 24 hours. The above aglycon components, free sugars or carboxylic acids resulting from treatment with the enzyme for hydrolysis, can be easily removed by conventional techniques such as cooling, liquid-liquid or solid-liquid extraction, or column adsorption, or a combination of these methods and normal phase chromatography. These steps allow efficient removal of contaminants in raw materials containing dimeric to pentameric proanthocyanidin oligomers or crude purification products therefrom, and improvement in purity of the target components, that is dimeric to pentameric proanthocyanidin oligomers.

In the third embodiment, dimeric to pentameric proanthocyanidin oligomers with a uniform polymerization degree can be obtained by separation and purification by polymerization degree from raw materials containing the proanthocyanidin oligomers or crude purification products therefrom by normal phase silica gel liquid chromatography using as a mobile phase a single solvent or a mixed solvent of two or more solvents selected from the group consisting of an ester solvent, a ketone solvent, a hydrocarbon solvent, an ether solvent and an alcohol solvent. To the above normal phase silica gel liquid chromatography, either a method using open column chromatography or that using high performance liquid chromatography can be applied. A solvent or water is removed from the solution containing dimeric to pentameric proanthocyanidin oligomers, and then the residue is dissolved in a mobile phase or in an organic solvent soluble in a mobile phase. When raw materials or crude purification products therefrom are solid, they are directly dissolved in a mobile phase or in an organic solvent soluble in a mobile phase. If necessary, they are filtered through a membrane filter or the like and then charged into a column. Upon elution of a target component, isocratic elution applying no concentration gradient on a mobile phase is preferred in view of simplification of operation. Examples of a preferable mobile phase in isocratic elution include mixed solvents, such as hexane/methanol/ethyl acetate, hexane/acetone, hexane/methanol/tetrahydrofuran/acetic acid, hexane/methanol/tetrahydrofuran/formic acid, hexane/methanol/methyl acetate/acetic acid, hexane/methanol/methyl acetate, and hexane/methyl acetate/acetone.

The purification process of the third embodiment enables efficient removal of contaminants, that is, monomers constituting proanthocyanidins, such as (+)-catechin, (+)-gallocatechin, (−)-epicatechin and (−)-epigallocatechin, and hexameric or higher order proanthocyanidin polymers; and enables separation and purification by polymerization degree of target components, that is, dimeric to pentameric proanthocyanidin oligomers.

The purification processes of the first to third embodiments in the present application may be freely selected, repeated, or combined depending on raw materials to be used as an extraction source, target purity and the like.

To purify dimeric to pentameric proanthocyanidin oligomers, combining two or more purification processes of the first to third embodiments is preferred. To purify dimeric to pentameric proanthocyanidin oligomers with a uniform polymerization degree, combining a purification process of the first embodiment and/or that of the second embodiment, and that of the third embodiment is preferred. Moreover, these processes may be combined with other known processes. When the purification processes are combined, the steps to be used and the order thereof may be freely selected.

By these processes, dimeric to pentameric proanthocyanidin oligomers, dimeric proanthocyanidins, and trimeric proanthocyanidins with highpurity (purity of 90(w/w) % or more) can be efficiently obtained.

Dimeric to pentameric proanthocyanidin oligomers, dimeric proanthocyanidins, and trimeric proanthocyanidins purified by the purification processes of this embodiment can be used as raw materials for manufacturing foods, cosmetics, drugs or the like.

BRIEF DESCRIPTION OF THE DRAWINGS

in FIG. 3.
[7]–[11] Dimer fractions corresponding to fraction Nos.
in FIG. 3.
[12]–[20] Trimer fractions corresponding to fraction Nos.
in FIG. 3.

in FIG. 5.
[5]–[9] Dimer fractions corresponding to fraction Nos.
in FIG. 5.
[10]–[15] Trimer fractions corresponding to fraction Nos.
in FIG. 5.

Figure 1:
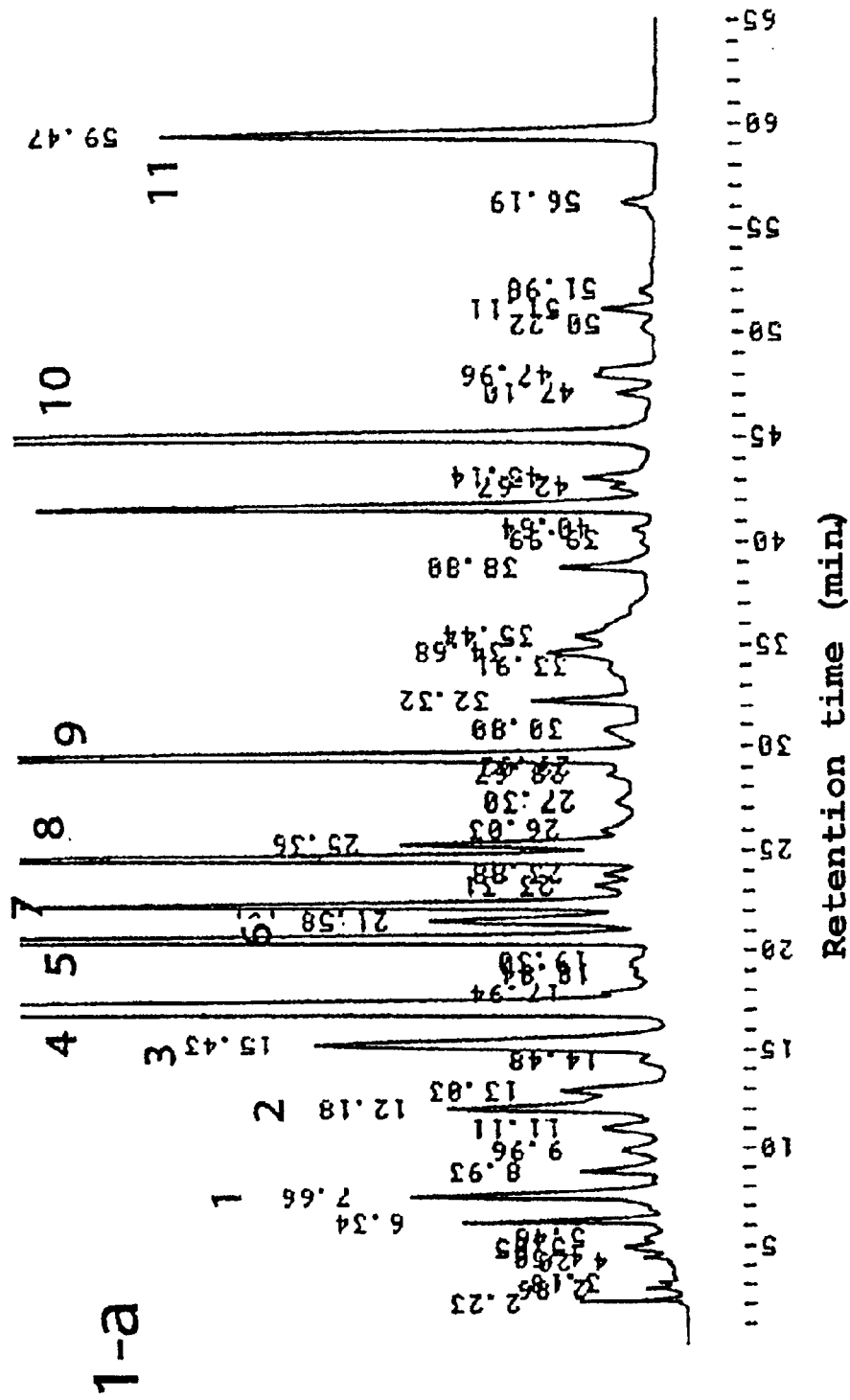
FIG. 1 shows the result of reversed phase liquid chromatography. Symbols in FIG. 1 denote the following.
1. PB1
2. (+)-catechin
3. PB2
4. chlorogenic acid
5. caffeic acid
6. PC1
7. (−)-epicatechin
8. p-coumaric acid ester
9. p-coumaric acid
10. phlorizin
11. phloretin
Figure 1:
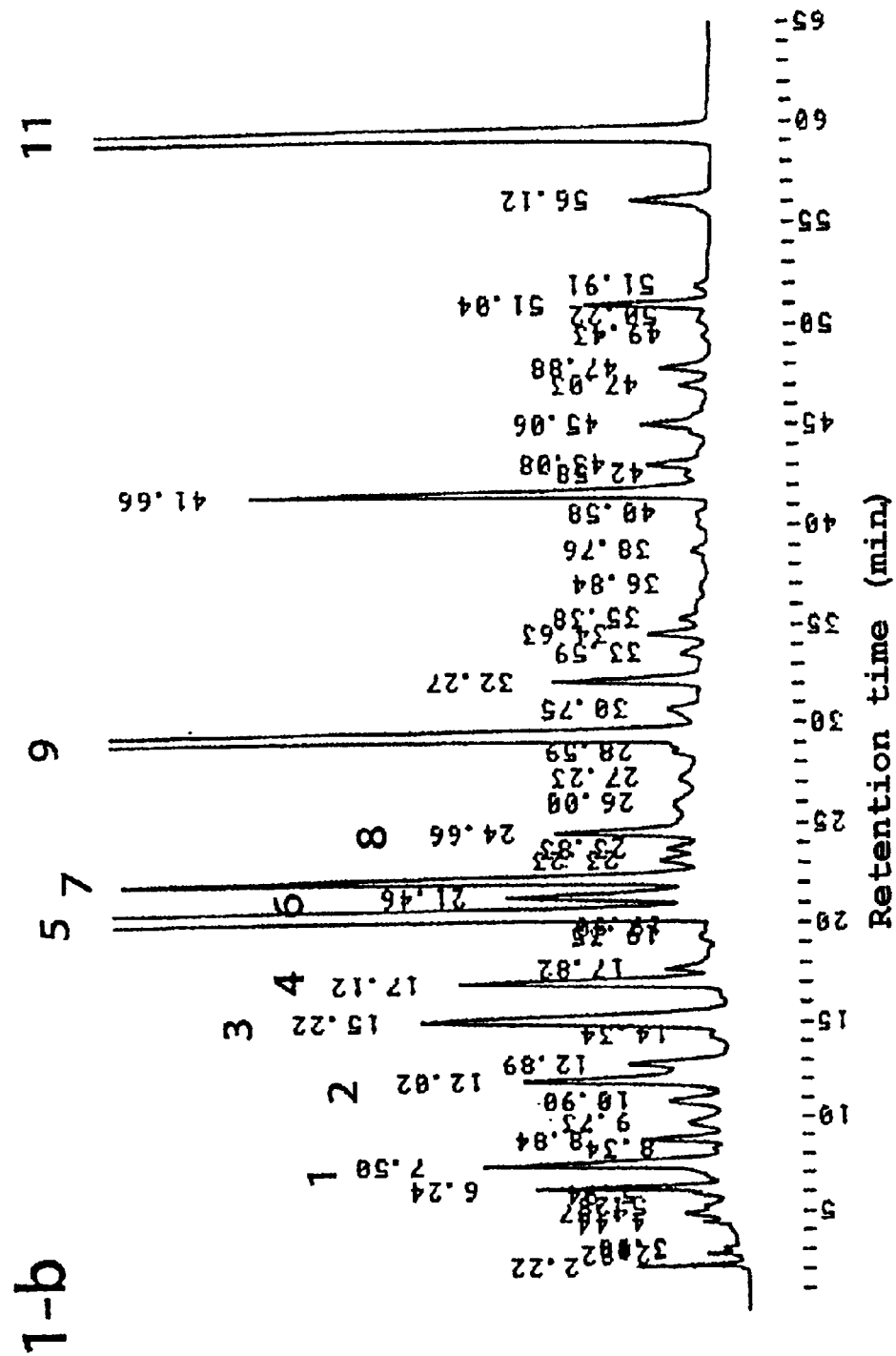
Figure 1:
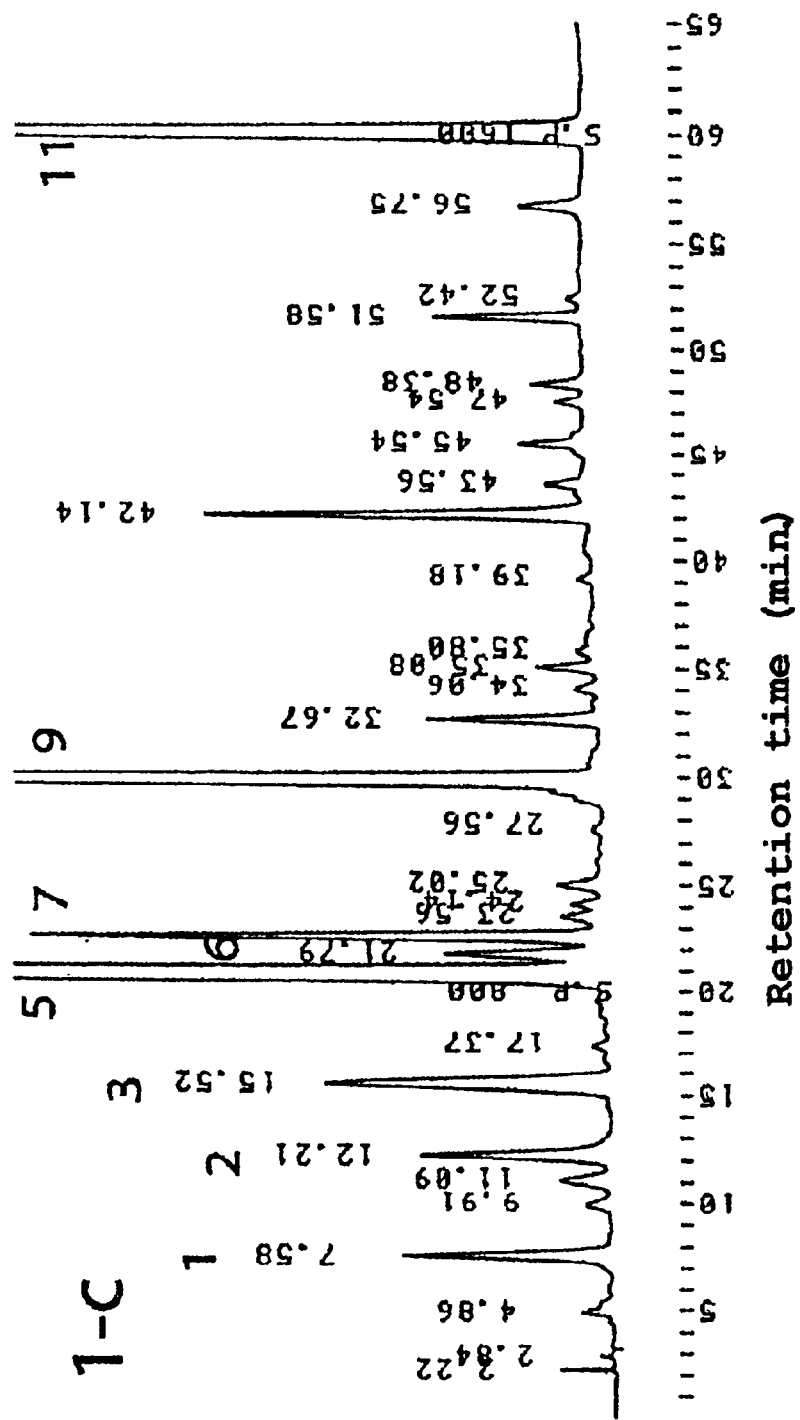
Figure 1:
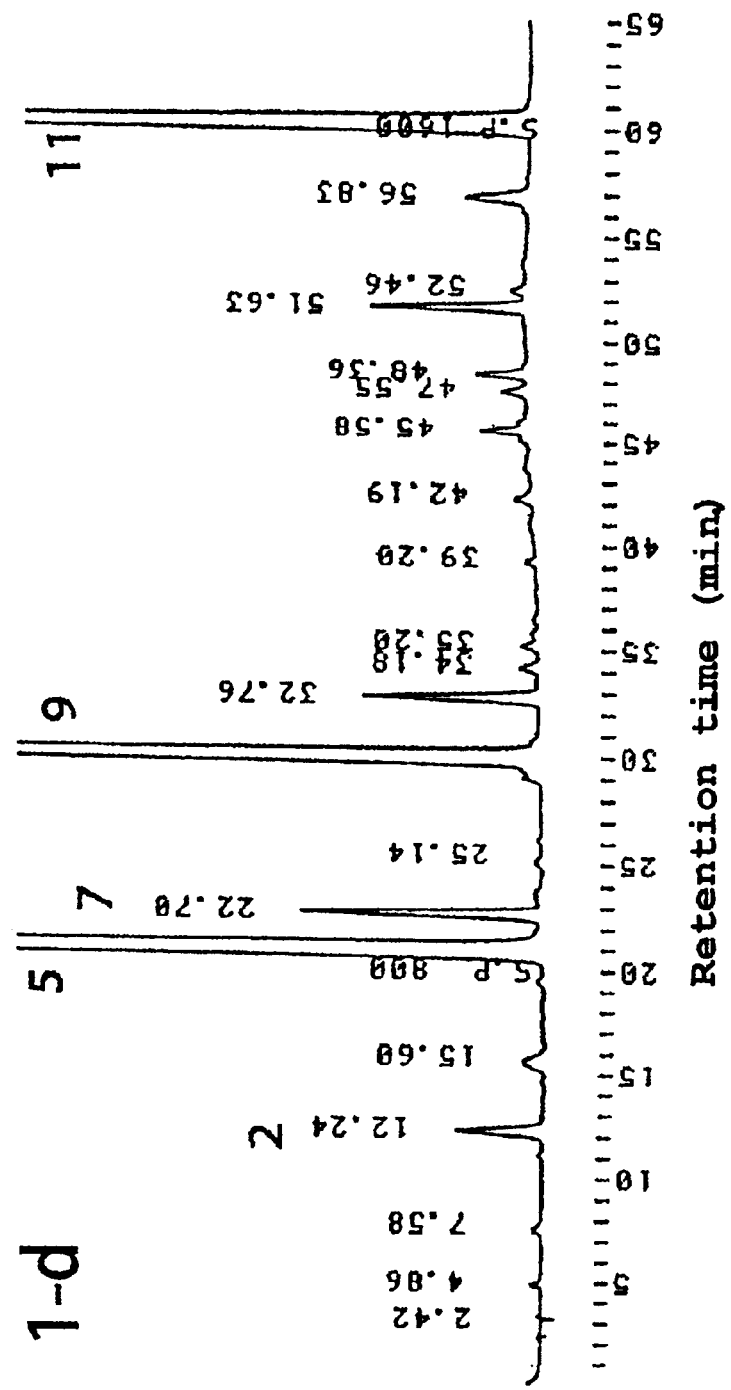

This specification includes part or all of the contents disclosed in the specification and/or drawings of Japanese Patent Application No. 11-116380 which is a priority document of the present application.

BEST MODE FOR CARRYING OUT THE INVENTION

Next, the present invention will be further described with examples, but is not limited by any of these examples or the like.

EXAMPLE 1

Purification by Solid-liquid Extraction (A)

300 ml of methyl acetate was added to 30 g of the proanthocyanidin fraction obtained in Reference Example 1, and then solid-liquid extraction was performed at room temperature for 1 hour. Extraction was performed twice in total, two extracts resulting from the extraction were mixed and then subjected to filtration. Then, the residue from the extraction was washed with a small amount of methyl acetate. The methyl acetate extracts and the washing were combined and concentrated under reduced pressure. A small amount of distilled water was added thereto, and concentration under reduced pressure was performed again and the extracted component was dissolved in an aqueous solution. The resulting aqueous solution was freeze-dried to give 17.5 g of a methyl acetate extract as a powder. Further, the residue from the extraction was dried to give 12.5 g of a non-extract from methyl acetate extraction as a powder. The contents of dimeric and trimeric proanthocyanidin components contained in both powder products were determined by reversed phase liquid chromatography as described in Reference Example 2. The determined dimeric proanthocyanidin components were procyanidin B1 (epicatechin-(4β→8)-catechin; hereinafter abbreviated as PB1) and procyanidin B2 (epicatechin-(4β→8)-epicatechin; herein after abbreviated as PB2). The trimer component determined was procyanidin C1 (epicatechin-(4β→8)-epicatechin-(4β→8)-epicatechin; hereinafter abbreviated as PC1). Table 1 shows the results of extraction with methyl acetate as well as yields(%) of a solid content.

the ratio is 95:5), and thus solvents for solid-liquid extraction were prepared. The organic solvent miscible with methyl acetate used in these various solvents was methanol, ethanol, propanol, butanol, ethyl formate, ethyl acetate, acetone, acetonitrile, tetrahydrofuran, hexane or acetic acid. 10 ml of the solvent for extraction was added to 1 g each of the proanthocyanidin fraction, obtained in Reference Example 1, and the mixture was subjected to solid-liquid extraction at room temperature for 1 hour (single extraction). After the removal of solid components from the extract by centrifugation, a certain amount of the extract was diluted 100 fold with distilled water (0.01→1 ml). Then the contents of PB1, PB2 and PC1 were determined by reversed phase liquid chromatography described in Reference Example 2. Simultaneously, 1 ml of each of the extracts was sampled to remove the solvents, and then freeze-dried, thereby deter-

TABLE 1

|  | Yield (g) | Yield of solid content (%) | PB1 Content (g) | PB1 Yield (%) | PB2 Content (g) | PB2 Yield (%) | PC1 Content (g) | PC1 Yield (%) | PB1 + PB2 + PC1 Content (g) | PB1 + PB2 + PC1 Yield (%) | PB1 + PB2 + PC1 Purity (%) |
|---|---|---|---|---|---|---|---|---|---|---|---|
| Sample before extraction | (30.0) |  | (1.22) |  | (4.34) |  | (1.96) |  | (7.52) |  | (25.1) |
| Methyl acetate extract | 17.5 | 58.3 | 1.16 | 95.1 | 4.03 | 92.8 | 1.65 | 84.2 | 6.84 | 91.0 | 39.1 |
| Non-extract from methyl acetate extraction | 12.5 | 41.7 | 0.06 | 4.9 | 0.31 | 7.2 | 0.31 | 15.8 | 0.68 | 9.0 | 5.4 |

As shown in Table 1, selective extraction and improvement of purity of proanthocyanidin oligomer components represented by PB1, PB2 and PC1 were efficiently achieved by solid-liquid extraction with methyl acetate.

EXAMPLE 2

Purification by Solid-liquid Extraction (B)

Methyl acetate and various solvents were mixed at a volume ratio of 9:1 (in the case of methyl acetate: hexane, mining the amount of a solid extract. Table 2 shows the extraction efficiencies and yields (%) of a solid content for PB1, PB2 and PC1 in the extract from solid-liquid extraction with each extraction solvent. And also, as a comparative example, solid-liquid extraction with ethyl acetate only was performed in a manner similar to that described above (except that 20 ml of ethyl acetate was used for 2 g of the proanthocyanidin fraction). Table 2 also shows the results from the comparative experiment.

TABLE 2

| Solvent for extraction | Yield of solid content (%) | PB1 (mg) | PB2 (mg) | PC1 (mg) | PB1 + PB2 + PC1 Amount of extract (mg) | PB1 + PB2 + PC1 Yield (%) | PB1 + PB2 + PC1 Purity (%) |
|---|---|---|---|---|---|---|---|
| Untreated with solvent for extraction | (100) | 36.4 | 136.1 | 63.0 | 235.5 | (100) | 23.6 |
| Ethyl acetate (Comparative Example) | 9.8 | 6.2 | 24.3 | 7.0 | 37.5 | 15.1 | 38.3 |
| 100% methyl acetate | 39.9 | 25.9 | 87.7 | 31.1 | 144.7 | 61.5 | 36.3 |
| Methyl acetate/methanol (9/1) | 82.8 | 39.5 | 137.1 | 62.7 | 239.3 | 101.6 | 28.9 |
| Methyl acetate/ethanol (9/1) | 80.5 | 39.8 | 140.1 | 64.6 | 244.4 | 103.8 | 30.4 |
| Methyl acetate/propanol (9/1) | 77.2 | 38.9 | 134.0 | 62.4 | 235.3 | 99.9 | 30.5 |

TABLE 2-continued

|  | Yield of solid content (%) | PB1 (mg) | PB2 (mg) | PC1 (mg) | PB1 + PB2 + PC1 | | |
|---|---|---|---|---|---|---|---|
| Solvent for extraction | | | | | Amount of extract (mg) | Yield (%) | Purity (%) |
| Methyl acetate/butanol (9/1) | 79.0 | 38.4 | 136.6 | 62.7 | 237.7 | 100.9 | 30.1 |
| Methyl acetate/ ethyl formate (9/1) | 40.0 | 26.3 | 89.9 | 31.1 | 147.3 | 62.5 | 36.8 |
| Methyl acetate/ ethyl acetate (9/1) | 39.6 | 25.4 | 86.6 | 30.1 | 142.1 | 60.3 | 35.9 |
| Methyl acetate/acetone (9/1) | 56.1 | 33.5 | 120.7 | 50.2 | 204.4 | 86.8 | 36.5 |
| Methyl acetate/ acetonitrile (9/1) | 59.3 | 35.8 | 123.2 | 51.3 | 210.4 | 89.3 | 35.5 |
| Methyl acetate/ tetrahydrofuran (9/1) | 83.7 | 34.4 | 120.1 | 51.3 | 205.8 | 87.4 | 24.6 |
| Methyl acetate/ acetic acid (9/1) | 70.5 | 38.3 | 131.1 | 56.5 | 225.9 | 95.9 | 32.1 |
| Methyl acetate/hexane (95/5) | 15.7 | 10.7 | 41.0 | 9.9 | 61.6 | 24.8 | 39.2 |

EXAMPLE 3

Purification by Solid-liquid Extraction (C)

Methyl acetate and ethyl acetate were mixed at a volume ratio as shown in Table 3, and then solid-liquid extraction was performed. 10 ml each of solvents for extraction data respective volume ratio was added to 1 g of the proanthocyanidin fraction obtained in Reference Example 1, followed by solid-liquid extraction at 30° C. for 1.5 hours. This step was repeated three times. These extracts were combined, concentrated under reduced pressure, and freeze-dried, thereby obtaining powder products (extract). The contents of PB1, PB2 and PC1 in the powder products were determined by reversed phase liquid chromatography described in Reference Example 2. Table 3 shows the results of extraction with a solvent at a respective volume ratio, including yields (%) of a solid content, amounts of the extract and yields of each of PB1, PB2 and PC1, and the amounts of the extract, yields (%) and purity of the total of PB1, PB2 and PC1.

TABLE 3

| Solvent for extraction | Yield of solid content (%) | PB1 (mg) (%) | PB2 (mg) (%) | PC1 (mg) (%) | PB1 + PB2 + PC1 | | |
|---|---|---|---|---|---|---|---|
| | | | | | Amount of extract (mg) | Yield (%) | Purity (%) |
| Untreated with solvent for extraction | 100 | 39.9 (100) | 153.4 (100) | 66.9 (100) | 260.2 | 100 | 26 |
| Ethyl acetate (Comparative Example) | 34.9 | 23.0 (57.6) | 90.4 (58.9) | 28.7 (42.9) | 142.1 | 54.6 | 40.7 |
| Ethyl acetate/ methyl acetate (9/1) | 39.2 | 25.8 (64.7) | 100.9 (65.8) | 32.3 (48.3) | 159 | 61.1 | 40.6 |
| Ethyl acetate/ methyl acetate (7/3) | 42.5 | 28.6 (71.7) | 110.2 (71.8) | 35.5 (53.1) | 174.3 | 67 | 41 |
| Ethyl acetate/ methyl acetate (5/5) | 46.5 | 31.0 (77.7) | 121.0 (78.9) | 39.9 (59.6) | 191.9 | 73.8 | 41.3 |
| Ethyl acetate/ methyl acetate (3/7) | 51 | 33.8 (84.7) | 130.1 (84.8) | 44.5 (66.5) | 208.4 | 80.1 | 40.9 |
| Ethyl acetate/ methyl acetate (1/9) | 51.6 | 33.0 (82.7) | 127.7 (83.2) | 45.4 (67.9) | 206.1 | 79.2 | 39.9 |
| Ethyl acetate/ methyl acetate (1/10) | 52.4 | 33.3 (83.5) | 128.9 (84.0) | 47.1 (70.4) | 209.3 | 80.4 | 39.9 |

As shown in Table 3, selective extraction and improvement of yields of proanthocyanidin oligomer components represented by PB1, PB2 and PC1 were efficiently achieved by solid-liquid extraction with a solvent for extraction containing methyl acetate.

EXAMPLE 4

Purification Combined with Enzymolysis Treatment

The polyphenol extract obtained in Reference Example 1 was treated with a commercially available enzyme preparation for food processing. Enzyme preparations used herein were a lipase preparation derived from the genus *Aspergillus* (Lipase Sankyo™, SANKYO CO., LTD.) and a hydrolase preparation (hydroxycinnamate hydrolase, (Seishin Co., Ltd.). 100 ml of the polyphenol extract has been previously adjusted to the pH value 5 with 5 mol/l NaOH and diluted 10 fold with distilled water, thereby obtaining a sample solution. 1 g each of the above lipase preparation and the above hydrolase preparation was added to 1L of the sample solution (final concentration: 0.1%), and an enzymatic reaction was allowed to proceed at 45° C. for 16 hours. The results of reversed phase liquid chromatography analysis described in Reference Example 2 performed on the sample solution before reaction and after reaction are shown in FIG. 1-*a* and 1-*b*, respectively. As shown in the figure, most of main contaminants, chlorogenic acid and phlorizin disappeared, and instead, free caffeic acid, p-coumaric acid and phloretin increased due to the enzymatic reaction above. Next, the solution after reaction was concentrated and then subjected to spray drying, thereby obtaining 20 g of powder. Then, 200 ml of methyl acetate was added thereto, and solid-liquid extraction was performed. A chromatogram of the methyl acetate extract is shown in FIG. 1-*c*. Proanthocyanidin polymers which appeared as an elevation on the baselines of FIGS. 1-*a* and 1-*b* were removed by solid-liquid extraction. Further, a small amount of distilled water was added to this extract, and then methyl acetate was removed by concentration under reduced pressure, thereby extracted components were dissolved in water. Ethyl acetate/n-hexane (8/2) (in an amount equivalent to the aqueous solution) was added to the obtained aqueous solution (50 ml) to perform liquid-liquid extraction. Chromatograms of the resulting organic solvent layer (upper layer) and aqueous layer (lower layer) are shown in FIG. 1-*d* and FIG. 1-*e*, respectively. Thus, part of the monomers constituting proanthocyanidins (catechin, epicatechin) and most of the main products from the previous enzyme treatment, free caffeic acid, p-coumaric acid, and phloretin, were removed into the organic solvent layer (FIG. 1-*d*). Most of the dimeric to pentameric proanthocyanidin oligomers represented by PB1, PB2 and PC1 remained in the aqueous layer after liquid-liquid extraction (FIG. 1-*e*). The finally obtained aqueous layer was concentrated and freeze-dried, thereby obtaining 5.7 g of powder. As a result of a series of steps, purity of PB1+PB2+PC1 in total solid contents was improved about 4 fold, from 11.5% to 40.3%. As described above, purity of target components, dimeric to pentameric proanthocyanidin oligomers can be efficiently improved by enzymolysis treatment on extracts from raw materials followed by a combination of multiple purification processes.

EXAMPLE 5

Purification by Normal Phase Liquid Chromatography (A)

Figure 2:
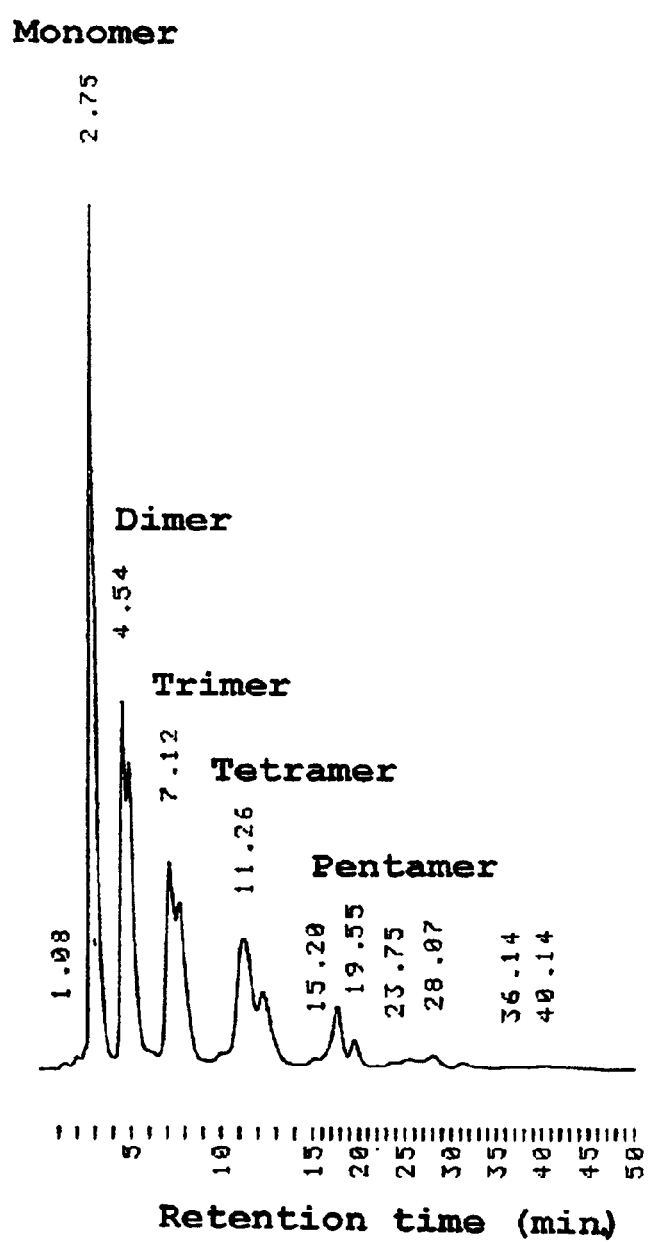
FIG. 2 shows the result of normal phase liquid chromatography.

100 ml of methyl acetate was added to 10 g of the proanthocyanidin fraction obtained in Reference Example 1 to perform solid-liquid extraction. The extract was concentrated under reduced pressure to a constant volume as a 20 ml concentrated liquid. Then normal phase liquid chromatography using silica gel as a filler was performed to separate components. Conditions for chromatography are as follows:

Column: Inertsil SIL™ (4.6 mm I.D.×150 mm, GL Science)
Mobile phase for isocratic separation: hexane/methanol/ethyl acetate (70/30/10)
Loading dose of a sample: 0.001 ml
Flow rate: 1.8 ml/min.
Detection: UV280 nm The obtained chromatogram is shown in FIG. 2. Under these conditions, proanthocyanidin oligomer components were separated by polymerization degree from dimer to higher order, and then eluted from the column. That is, it was confirmed that selective separation of oligomer components with a uniform polymerization degree, dimers, trimers, and the like, depending on each purpose, was achieved by normal phase liquid chromatography using silica gel as a filler.

Figure 3:
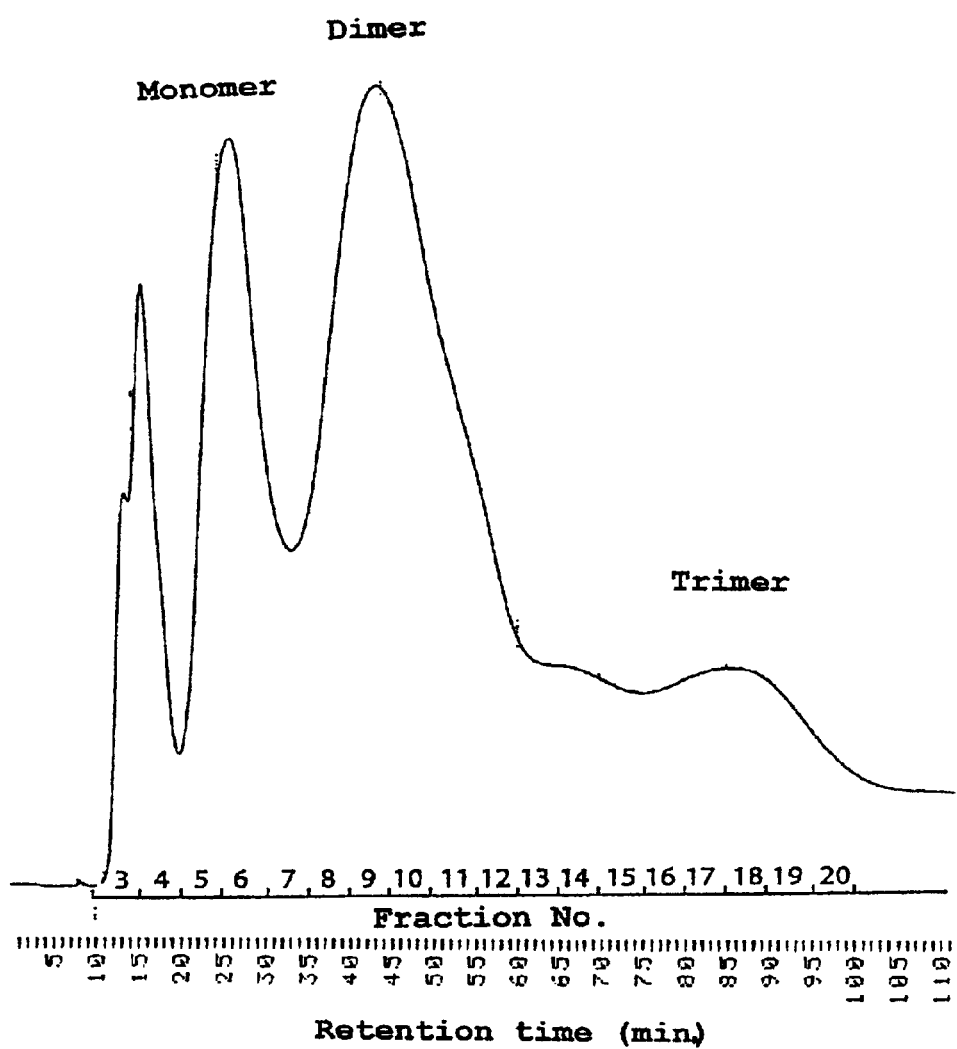
FIG. 3 shows the result of normal phase liquid chromatography.

Moreover, using the same concentrated liquid samples, a normal phase liquid chromatography fractionation was performed on the preparative scale. Conditions for the fractionation are as follows:

Silica gel filler: spherical multiporous silica gel (75 μm, 120A)
Column size: 6 mm I.D.×500 mm×2 columns
Mobile phase for isocratic separation: hexane/methanol/ethyl
acetate (70/30/10)
Loading dose of a sample: 0.5 ml
Flow rate: 3 ml/min.
Fractionation: 15 ml/5 min./1 fraction
Detection: UV280 nm As shown in FIG. 3, proanthocyanidin oligomers in the samples were also separated by polymerization degree even on the preparative scale.

Figure 4:
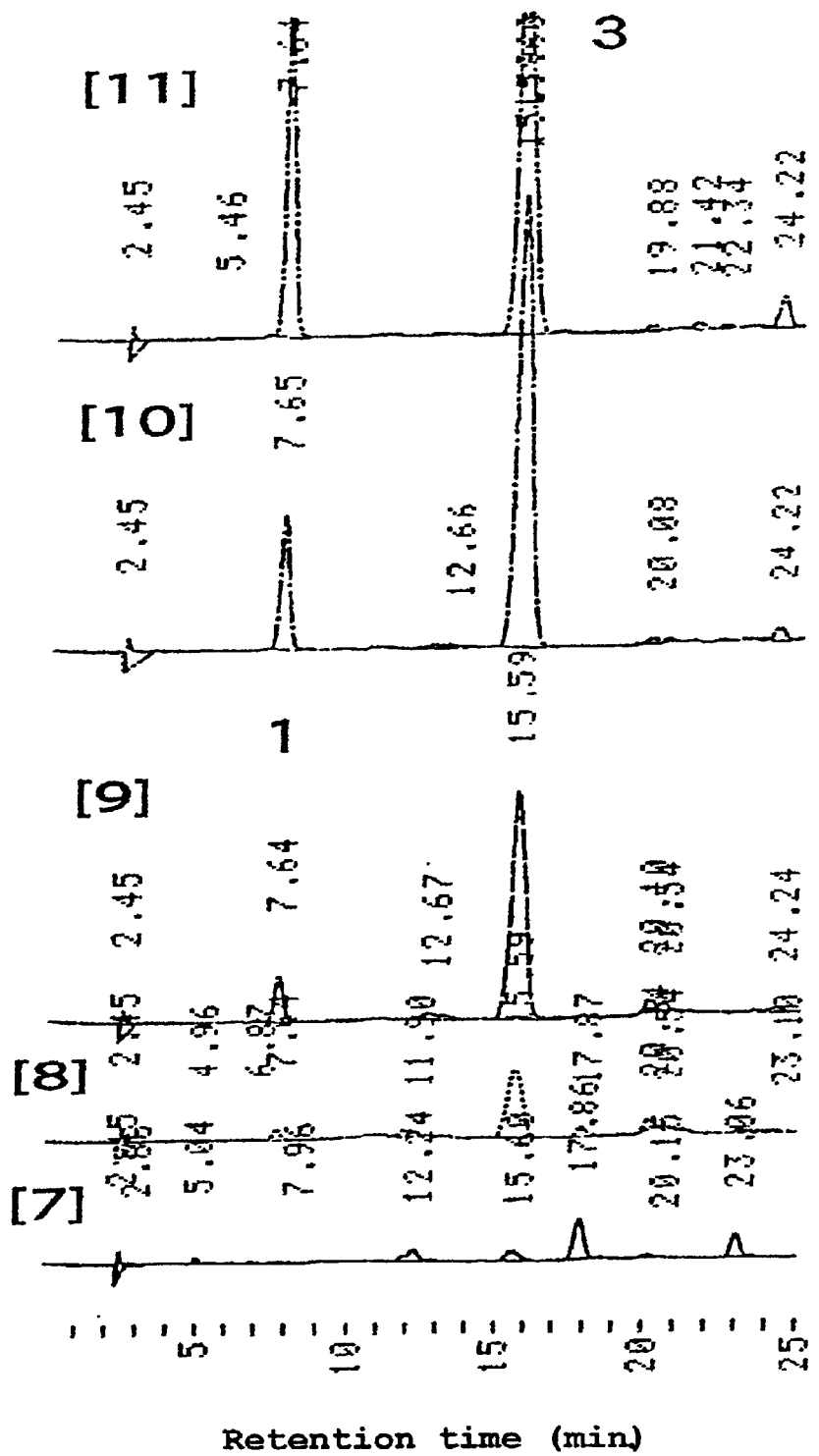
FIG. 4 shows the result of reversed phase liquid chromatography. Symbols in FIG. 4 denote the following.
1. PB1
2. (+)-catechin
3. PB2
4. PC1
5. (−)-epicatechin
[5], [6] Monomer fractions corresponding to fraction Nos.
Figure 4:
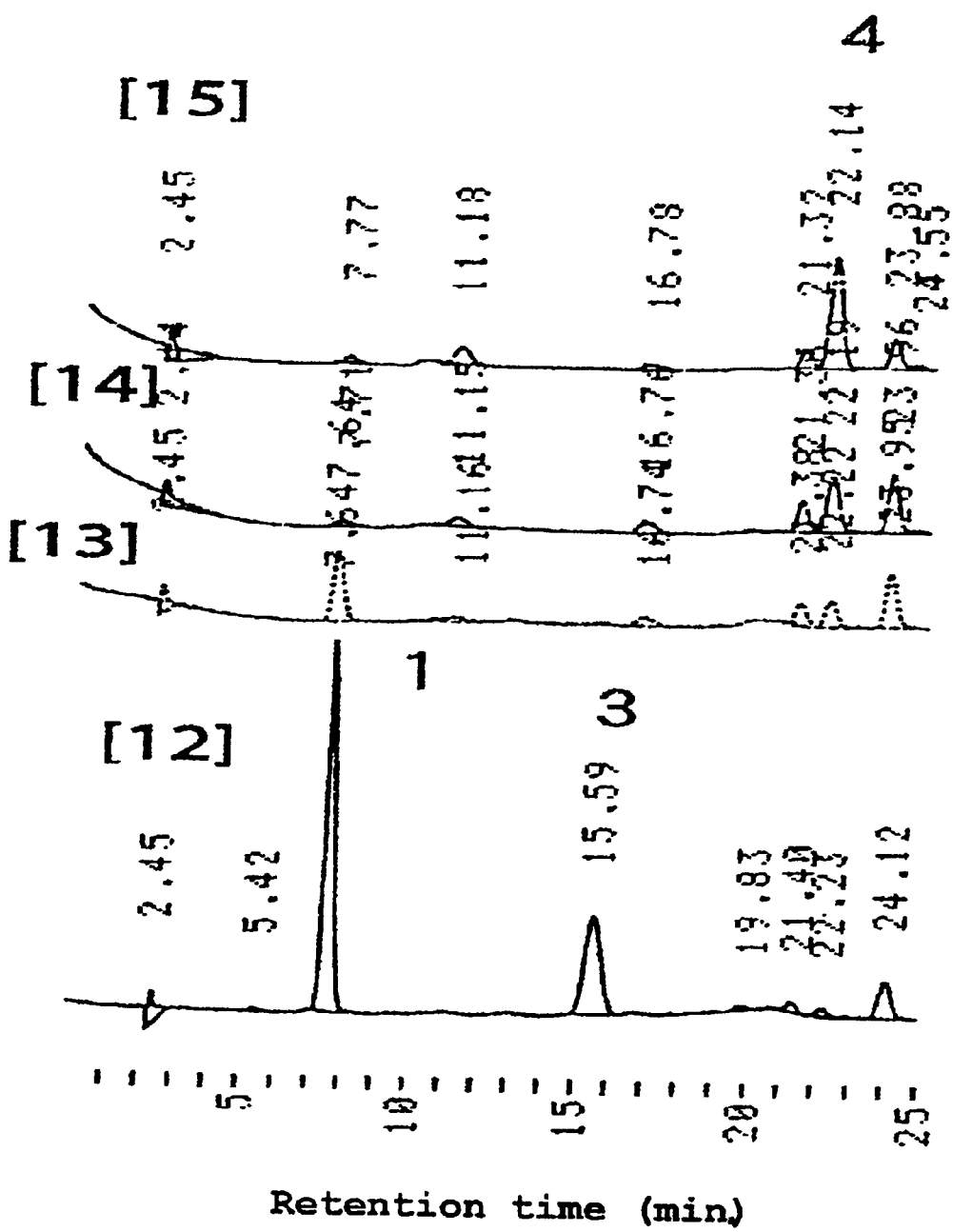
Figure 4:
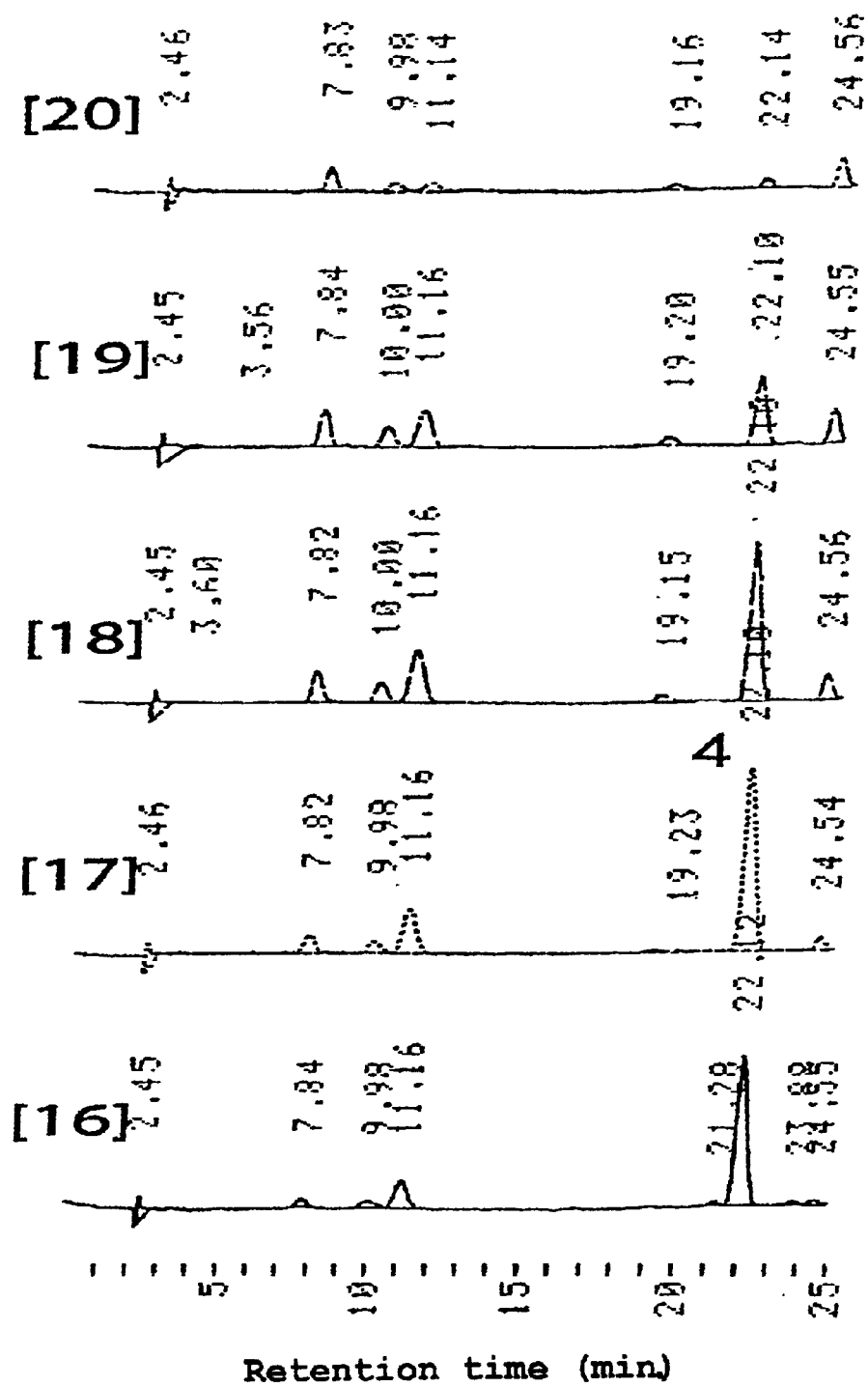

Subsequently, eluted fractions corresponding to monomers, dimers, and trimers on the chromatogram were sampled. Then, the constitution of oligomer components in each eluted fraction was examined using reversed phase liquid chromatography described in Reference Example 2. As shown in FIG. 4–[5] and FIG. 4–[6], the monomer fractions were mainly composed of catechin and epicatechin, as shown in FIGS. 4–[7] to [11], the dimer fractions were mainly composed of PB1 and PB2, and as shown in FIGS. 4–[12] to [20], the trimer fractions were mainly composed of PC1. The separated fractions were each composed of oligomer components with a uniform polymerization degree.

Purity of the purified dimeric and trimeric proanthocyanidin products obtained above were 93 and 92 (w/w)%, respectively.

EXAMPLE 6

Purification by Normal Phase Liquid Chromatography (B)

Figure 5:
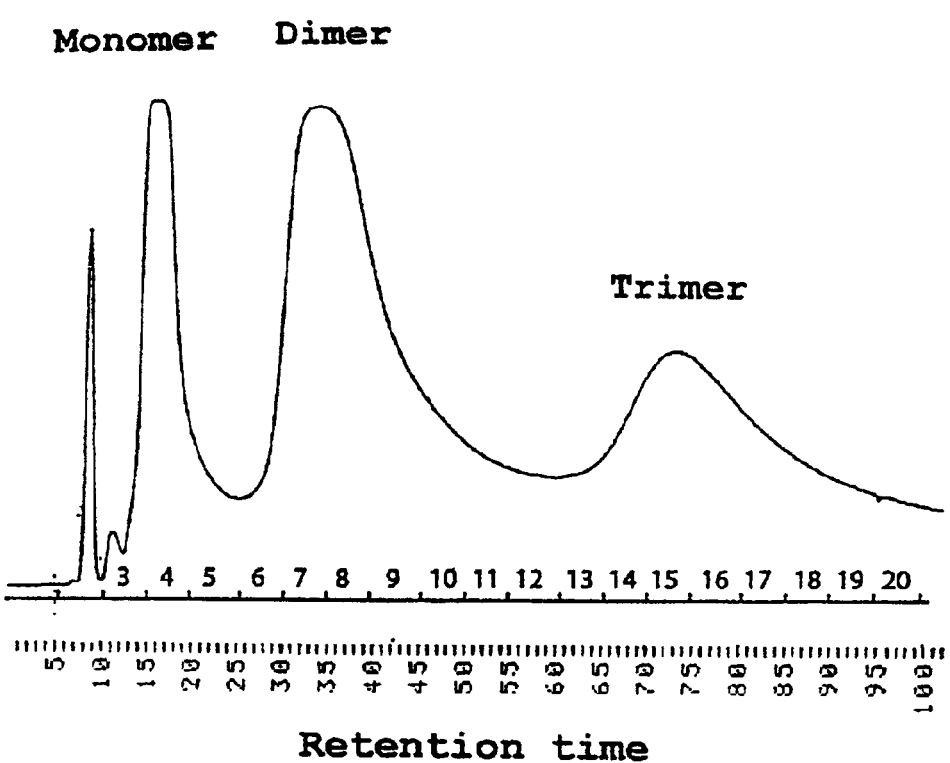
FIG. 5 shows the result of normal phase liquid chromatography.
Figure 6:
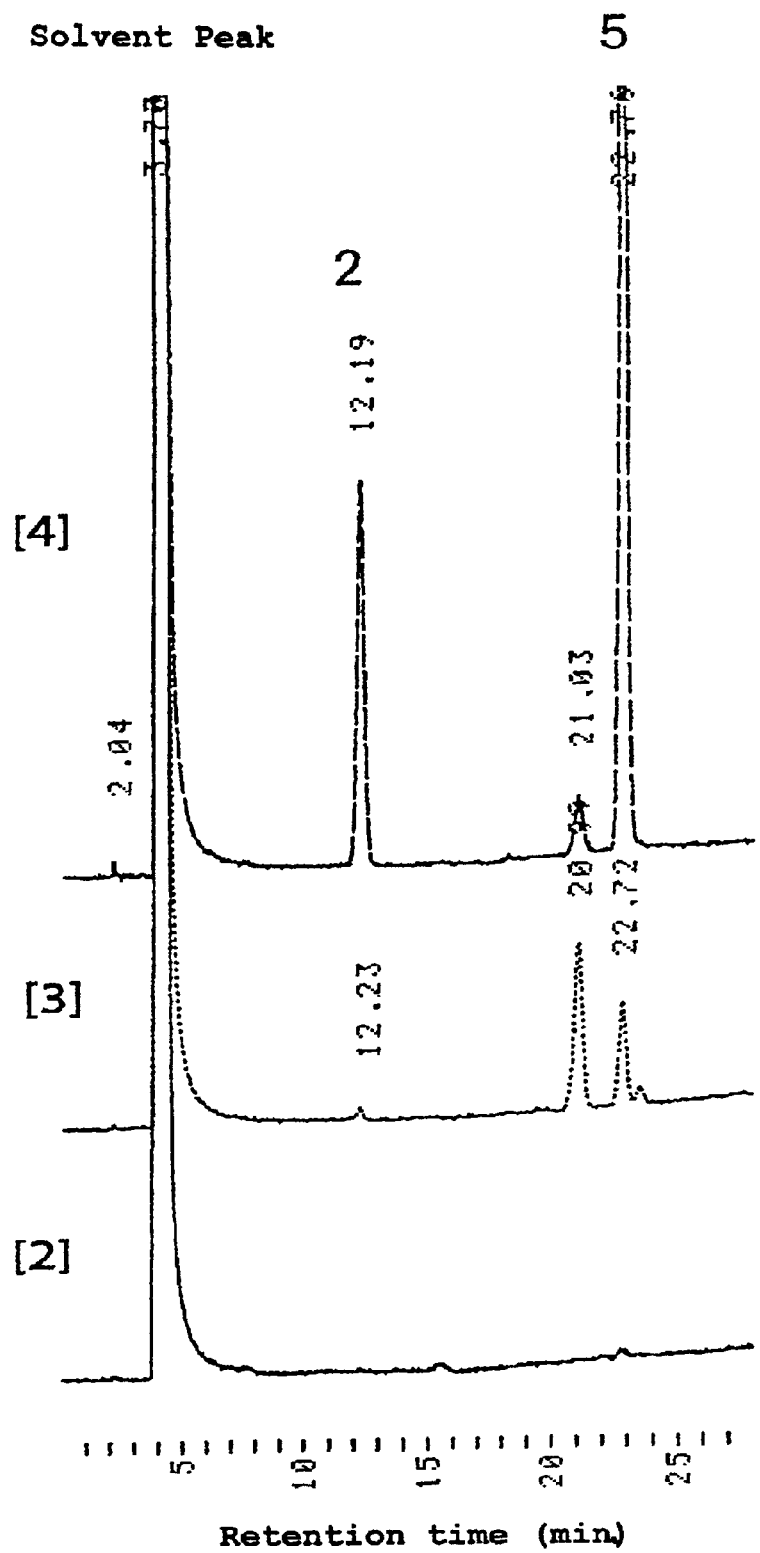
FIG. 6 shows the result of reversed phase liquid chromatography. Symbols in FIG. 6 denote the following.
1. PB1
2. (+)-catechin
3. PB2
4. PC1
5. (−)-epicatechin
[2]–[4] Monomer fractions corresponding to fraction Nos.
Figure 6:
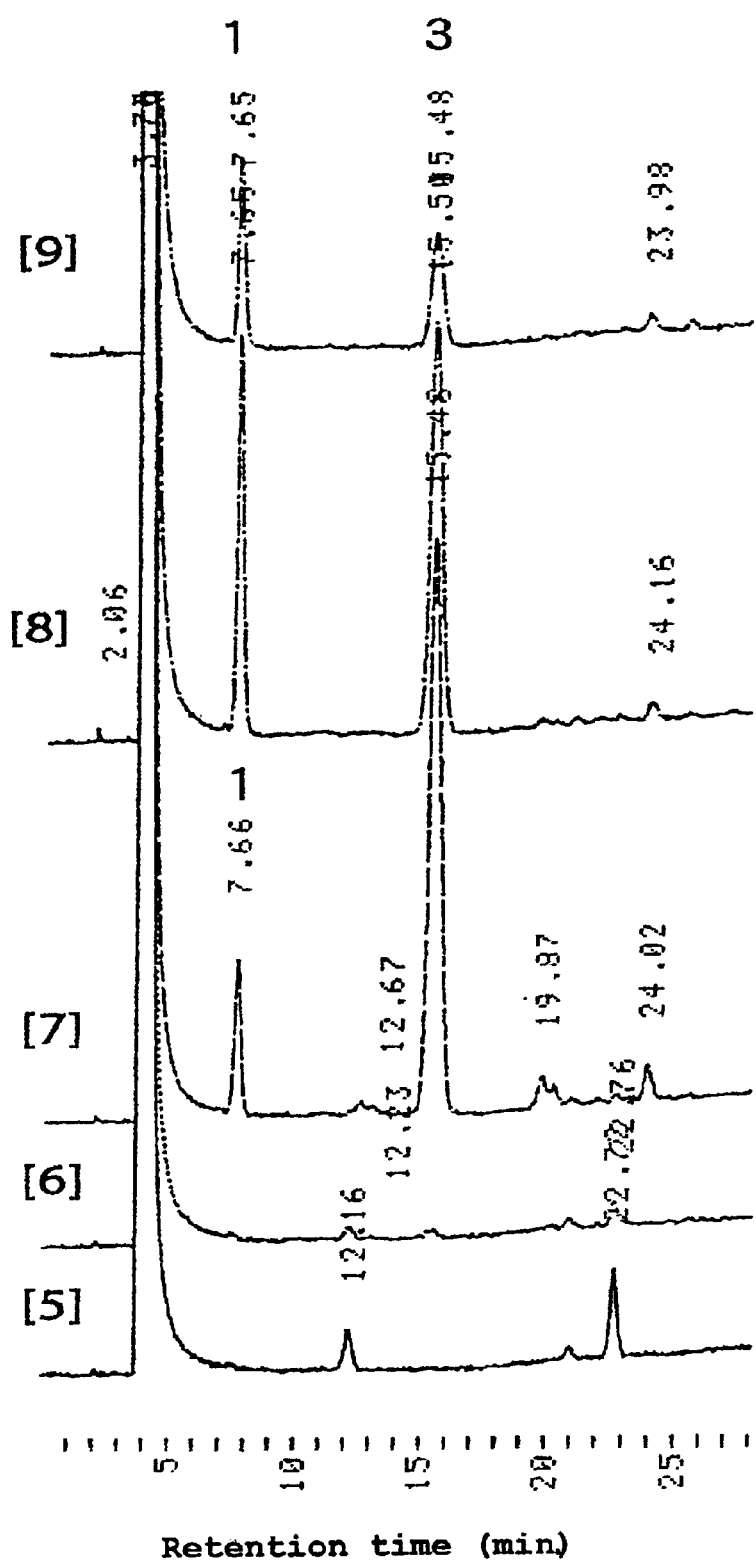
Figure 6:
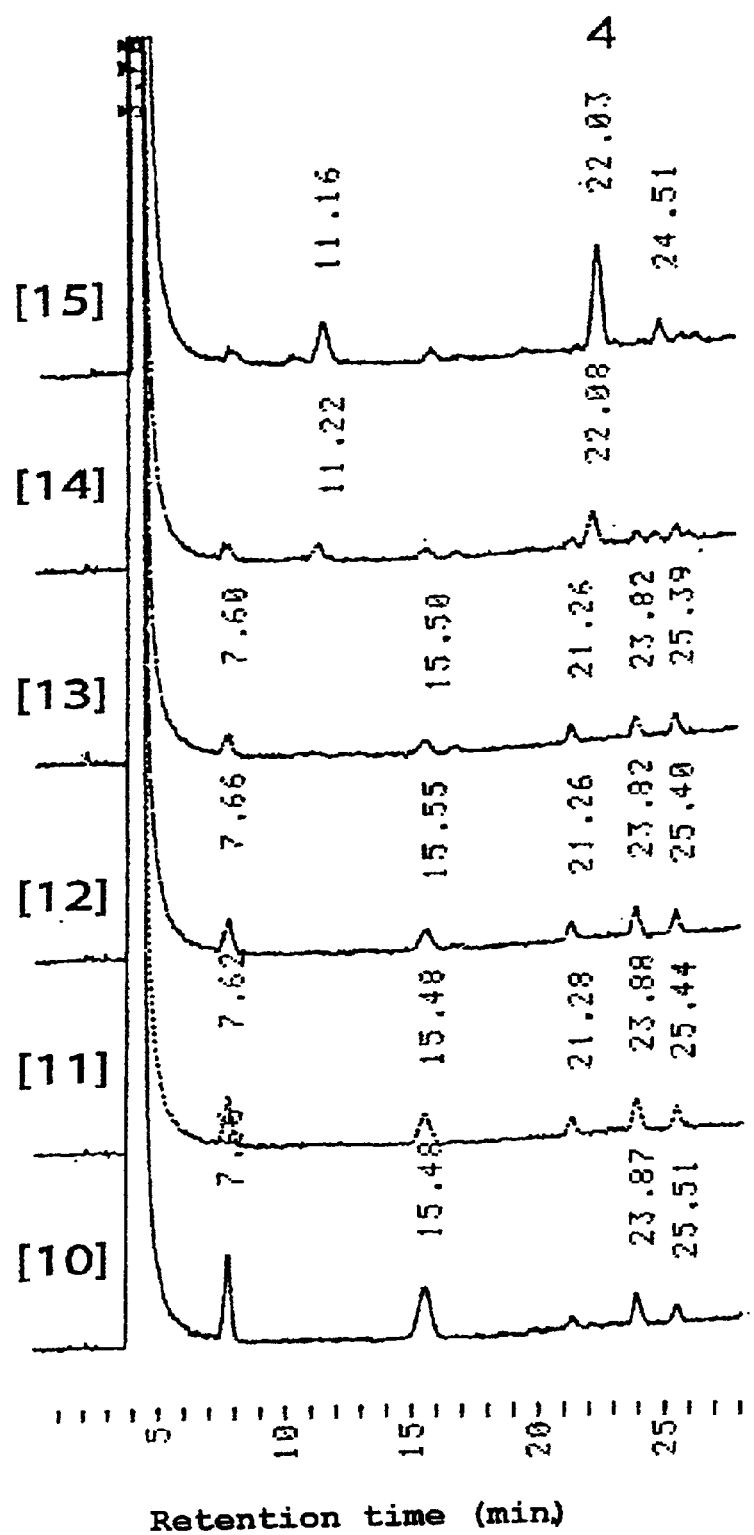

Using the concentrated liquid sample obtained in Example 5, a normal phase liquid chromatography fractionation was performed. Conditions for the fractionation are as follows:

Silica gel filler: spherical multiporous silica gel (75 μm, 120A)
Column size: 6 mm I.D.×500 mm×2 columns
Mobile phase for isocratic separation: hexane/acetone (40/60)
Loading dose of a sample: 0.05 ml
Flow rate: 3 ml/min.
Fractionation: 15 ml/5 min./1 fraction
Detection: UV280 nm FIG. 5 shows the obtained chromatogram. Further, eluted fractions corresponding to monomers, dimers, and trimers on the chromatogram were sampled. Then, the constitution of oligomer components in each eluted fraction was examined using reversed phase liquid chromatography described in Reference Example 2. As shown in FIGS. 6–[2] to [4], the monomer fractions were mainly composed of catechin and epicatechin, as shown in FIGS. 6–[5] to [9], the dimer fractions were mainly composed of PB1 and PB2, and as shown in FIGS. 6–[10]) to [15], the trimer fractions were mainly composed of PC1. Similar to Example 5, the separated fractions were each composed of oligomer components with a uniform polymerization degree.

Purity of the purified dimeric and trimeric proanthocyanidin products obtained above were 95 and 93 (w/w)%, respectively. (Reference Example 1) Preparation of a proanthocyanidin fraction from an apple fruit.

A polyphenol extract and a proanthotyanidin fraction were prepared from apple fruits according to the method described hi in Rapid Communication of Mass Spectrometry, 11, 31–36 (1997). Immature apple fruits (3 kg) of a major variety "Fuji" were used as raw materials. Fruits were crushed while adding 3 g of potassium metabisulfite thereto and squeezed to obtain the juice. The juice was centrifuged and filtered for clarification, thereby obtaining 1.8 L of clear juice. Next, the juice was added to a Sepabeads Sp-850™ (Nippon Rensui)-filled column (25 mm I.D. ×285 mm), allowing polyphenol components in the juice to adsorb thereto. After sugars and organic acids present in the juice were removed by washing with 300 ml of distilled water, the polyphenol components were eluted with 200 ml of a 80% aqueous ethanol solution. Further, the collected eluate was concentrated to 65 ml under reduced pressure, so that the polyphenol extract was obtained. The polyphenol extract (25 ml) was further added to a TSK-GEL toyopearl HW-40EC™ (TOSOH)-filled column (25 mm I.D.×285 mm) and the column was washed with 200 ml of distilled water, so that most of the contaminants, phenol carboxylic acids, were removed. Then 250 ml of a 40% aqueous ethanol solution was added to the column so that other low molecular polyphenols were eluted. Subsequently, 100 ml of a 60% aqueous acetone solution was added to the column, thereby eluting and recovering most of the proanthocyanidins. Here, part of the dimeric to pentameric proanthocyanidin oligomers was mixed in the eluate from elution with a 40% aqueous ethanol solution. Thus, eluate was subjected to de-ethanol by concentration under reduced pressure, the concentrate was further added to Sep-pak C18ENV™ column (waters), thereby re-purifying and recovering only the mixed-in proanthocyanidin components. The recovered solution and the eluate from elution with a 60% aqueous acetone solution were mixed, concentrated under reduced pressure, and freeze-dried, thereby obtaining a proanthocyanidin fraction (clear juice 1.8L→8 g). A mass spectrometric analysis revealed that this fraction consisted of monomeric to 15-meric proanthocyanidins. According to the demand, this step was performed on a larger scale so that a polyphenol extract or a proanthocyanidin fraction was prepared in an amount required in each Example. (Reference Example 2) Polyphenol analysis The composition of polyphenol components in various samples described in the Examples was analyzed by reversed phase liquid chromatography under the following conditions, according to the demand.
Column: Inertsil ODS-3™ (4.6×15 mm, GL Science)
Eluent: A) 0.1 mol/1 phosphate buffer (pH 2)/methanol (8/2)
B) 0.1 mol/1 phosphate buffer (pH 2)/methanol (5/5)
Gradient elution conditions: 0→10 min. (100% A), 10 min.→50 min. (100% A→100% B), 50 min.→65 min. (100% B)
Loading dose of a sample: 10 μl
Flow rate: 1 ml/min.
Detection: 280 nm (Reference Example 3) Analysis of the distribution in polymerization degree of proanthocyanidin oligomers The distribution in polymerization degree of proanthocyanidin oligomers in the powder products obtained in Example 1 from the extract or the non-extract from extraction with methyl acetate was analyzed by gel permeation chromatography.
Conditions for analysis are as follows:
Column: TSK-GEL toyopearl HW-40F™ (2.5×95 cm, TOSOH)
Eluent: acetone/8 mol/1 urea (6/4)
Flow rate: 1.0 ml/min.
Fractionation: 3 ml/3 min./1 fraction (the initial 80 ml was discarded)
Detection: Colorimetry by addition of aphenol reagent (detected at VIS760 nm)

Figure 7:
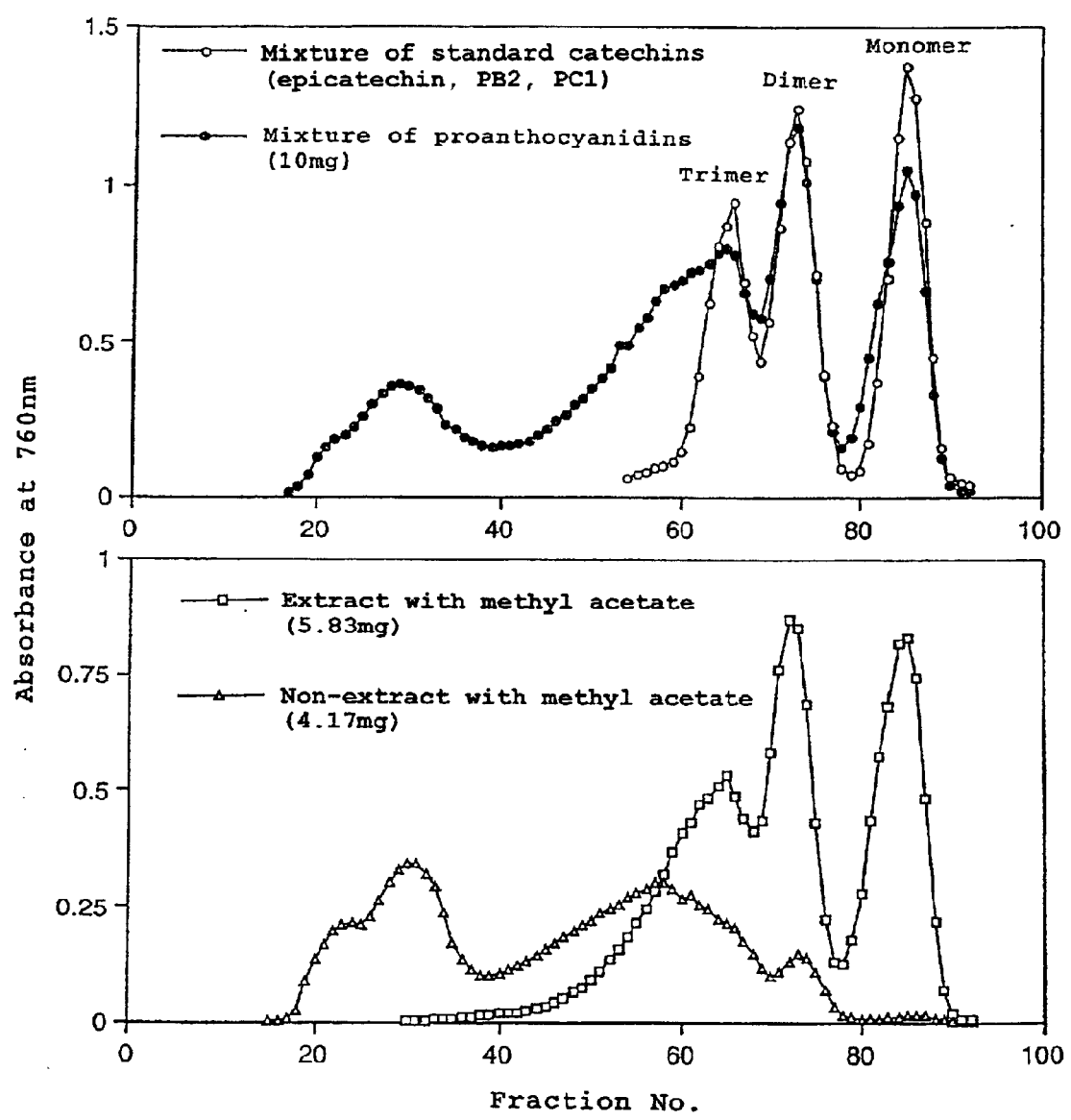
FIG. 7 shows the result of analyzing the distribution of polymerization degrees of proanthocyanidin oligomers.

Further, a mixture of standard catechins (2 mg each of epicatechin, PB2 and PC1), a proanthocyanidin mixture (10 mg), a powder product extracted with methyl acetate from the proanthocyanidin mixture (5.83 mg), and a powder product not extracted with methyl acetate from the same mixture (4.17 mg) were separately dissolved in 0.5 ml of an eluent and subjected to analysis. FIG. 7 shows the results.

As shown in FIG. 7, under the above conditions for analysis, proanthocyanidin oligomers in a sample were eluted in order of larger to smaller polymerization degrees based on the molecular sieve effect of a filler. Particularly trimer, dimer, and monomer components appeared as individual peaks on a chromatogram.

As shown in FIG. 7, the powder product extracted with methyl acetate consisted mainly of monomeric, dimeric and trimeric proanthocyanidin oligomer components. On the other hand, the powder product not extracted with methyl acetate consisted mainly of proanthocyanidin polymers components with large molecular weight.

All publications, patents and patent applications cited herein are incorporated herein by reference in their entirety.

What is claimed is:

1. A process for purification of dimeric to pentameric proanthocyanidin oligomers, which comprises extracting the proanthocyanidin oligomers from raw materials, which contain the proanthocyanidin oligomers or crude purification products therefrom, by a solid-liquid extraction method using methyl acetate as a liquid phase.

2. The process for purification of claim 1, wherein the raw materials are derived from a plant.

3. The process for purification of claim 1, wherein the liquid phase comprises an organic solvent miscible with methyl acetate.

4. The process for purification of claim 3, wherein the organic solvent miscible with methyl acetate is selected from the group consisting of an alcohol solvent, an ester solvent, a ketone solvent, a nitrile solvent, an ether solvent, a hydrocarbon solvent and a carboxylic acid solvent.

5. The process for purification of claim 3, wherein the organic solvent miscible with methyl acetate is selected from the group consisting of methanol, ethanol, propanol, butanol, methyl formate, ethyl formate, ethyl acetate, acetone, acetonitrile, tetrahydrofuran, hexane and acetic acid.

6. A process for purification of dimeric to pentameric proanthocyanidin oligomers which comprises pretreating with an enzyme for hydrolysis raw materials which contain the proanthocyanidin oligomers, crude purification products therefrom, or a solution containing one of these.

7. The process for purification of claim 6, wherein the raw materials are derived from a plant.

8. The process for purification of claim 6, wherein the solution is an aqueous solution containing a 10% or less organic solvent.

9. The process for purification of claim 8, wherein the organic solvent is an alcohol, ester, or ketone organic solvent.

10. The process for purification of claim 6, wherein the enzyme for hydrolysis is glycosidase or esterase.

11. The process for purification of claim 10, wherein the glycosidase is a single substance or a mixture of two or more substances selected from the group consisting of amylase, cellulase, glucanase, xylanase, glucosidase, dextranase, chitinase, galacturonase, lysozyme, galactosidase, mannosidase, fructofuranosidase, trehalase, glucosaminidase, pullulanase, ceramidase, fucosidase and agarase.

12. The process for purification of claim 10, wherein the esterase is a single substance or a mixture of two or more substances selected from the group consisting of carboxyesterase, arylesterase, lipase, acetylesterase, cholinesterase, pectinesterase, cholesterol esterase, chlorophyllase, lactonase, tannase and hydrolase.

13. A process for purification of dimeric to pentameric proanthocyanidin oligomers with a uniform polymerization degree which comprises:

selecting raw materials containing dimeric to pentameric proanthocyanidin oligomers or crude purification products therefrom;

separating and purifying said raw materials by normal phase silica gel liquid chromatography using as a mobile phase at least one solvent selected from the group consisting of an ester solvent, a ketone solvent, a hydrocarbon solvent, an ether solvent and an alcohol solvent.

14. The process for purification of claim 13, wherein the raw materials are derived from a plant.

15. The process for purification of claim 13, wherein mobile phase is a mixture of at least two of said solvents.

16. The process for purification of claim 13, wherein the ester solvent is selected from the group consisting of methyl formate, ethyl formate, propyl formate, isopropyl formate, butyl formate, isobutyl formate, methyl acetate, ethyl acetate, propyl acetate, isopropyl acetate, butyl acetate, isobutyl acetate, methyl propionate, ethyl propionate, propyl propionate, isopropyl propionate, butyl propionate, isobutyl propionate, methyl butyrate, ethyl butyrate, propyl butyrate, isopropyl butyrate, butyl butyrate and isobutyl butyrate.

17. The process for purification of claim 13, wherein the ketone solvent is selected from the group consisting of acetone, methyl ethyl ketone, methyl propyl ketone, methyl isopropyl ketone, methyl butyl ketone, methyl isobutyl ketone, methyl tert-butyl ketone, diethyl ketone, diisopropyl ketone, methyl vinyl ketone, cyclobutanone, cyclopentanone and cyclohexanone.

18. The process for purification of claim 13, wherein the hydrocarbon solvent is selected from the group consisting of pentane, hexane, heptane, octane, nonane, decane, nonadecane, cyclohexane, xylene and toluene.

19. The process for purification of claim 13, wherein the ether solvent is tetrahydrofuran or 1, 2-dimethoxyethane.

20. The process for purification of claim 13, wherein the alcohol solvent is selected from the group consisting of methanol, ethanol, propanol, isopropanol, butanol, sec-butanol and tert-butanol.

21. A process for purification of dimeric to pentameric proanthocyanidin oligomers comprising at least two processes for purification selected from claims 1, 6 and 13.

22. A purified dimeric to pentameric proanthocyanidin oligomer with a purity of 90 (w/w)% or more obtained by the process for purification of claim 1.

23. A purified dimeric to pentameric proanthocyanidin oligomer with a purity of 90 (w/w)% or more obtained by the process for purification of claim 6.

24. A purified dimeric to pentameric proanthocyanidin oligomer with a purity of 90 (w/w)% or more obtained by the process for purification of claim 21.

25. A purified dimeric proanthocyanidin with a purity of 90 (w/w)% or more obtained by the process for purification of claim 13.

26. A purified trimeric proanthocyanidin with a purity of 90 (w/w)% or more obtained by the process for purification of claim 13.

27. A process for purification of dimeric to pentameric proanthocyanidin oligomers with a uniform polymerization degree comprising a combination of the process for purification of claim 13, and at least one process selected from the group consisting of (i) a process for purification of dimeric to pentameric proanthocyanidin oligomers which comprises extracting the proanthocyanidin oligomers from raw materials, which contain the proanthocyanidin oligomers or crude purification products therefrom, by a solid-liquid extraction method using methyl acetate as a liquid phase, and (ii) a process for purification of dimeric to pentameric proanthocyanidin oligomers which comprises pretreating with an enzyme for hydrolysis raw materials which contain the proanthocyanidin oligomers, crude purification products therefrom, or a solution containing one of these.

28. A purified dimeric proanthocyanidin with a purity of 90 (w/w)% or more obtainable by the process for purification of claim 27.

29. A purified trimeric proanthocyanidin with a purity of 90 (w/w)% or more obtainable by the process for purification of claim 27.

30. A purified dimeric to pentameric proanthocyanidin oligomer with a purity of 90 (w/w)% or more.

31. A purified dimeric proanthocyanidin oligomer with a purity of 90 (w/w)% or more.

32. A purified trimeric proanthocyanidin oligomer with a purity of 90 (w/w)% or more.

* * * * *